United States Patent
Peng et al.

(10) Patent No.: US 9,890,193 B2
(45) Date of Patent: *Feb. 13, 2018

(54) COMPOUNDS HAVING TRIPLE ACTIVITIES OF THROMBOLYSIS, ANTITHROMBOSIS, AND RADICAL SCAVENGING, SYNTHESIS, AND USE THEREOF

(71) Applicant: Shanghai Lumosa Therapeutics Co., Ltd., Shanghai (CN)

(72) Inventors: Shi-Qi Peng, Beijing (CN); Ming Zhao, Beijing (CN); Jian-Hui Wu, Beijing (CN); Yu-Ji Wang, Beijing (CN); Qi-Qi Feng, Beijing (CN)

(73) Assignee: Shanghai Lumosa Therapeutics Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/956,723

(22) Filed: Dec. 2, 2015

(65) Prior Publication Data
US 2016/0083423 A1    Mar. 24, 2016

Related U.S. Application Data

(63) Continuation of application No. PCT/CN2014/079098, filed on Jun. 3, 2014.

(30) Foreign Application Priority Data

Jun. 5, 2013 (CN) .......................... 2013 1 0225330

(51) Int. Cl.
*A61K 38/06* (2006.01)
*A61K 38/07* (2006.01)
(Continued)

(52) U.S. Cl.
CPC .......... *C07K 5/0821* (2013.01); *A61K 47/545* (2017.08); *A61K 47/55* (2017.08);
(Continued)

(58) Field of Classification Search
None
See application file for complete search history.

(56) References Cited

U.S. PATENT DOCUMENTS 3,846,573 A * 11/1974 Okumura ............. C07D 217/26
  252/403
7,186,715 B2    3/2007 Briner et al.
(Continued)

FOREIGN PATENT DOCUMENTS

CN    101190895 A    6/2008
CN    101190941 A    6/2008
(Continued)

OTHER PUBLICATIONS

International Search Report for Application No. PCT/CN2014/079098 dated Sep. 2, 2014, 2 pages.
(Continued)

*Primary Examiner* — Kevin S Orwig
(74) *Attorney, Agent, or Firm* — Perkins Coie LLP; Viola T. Kung

(57) ABSTRACT

The present invention relates to a compound simultaneously having triple activities of thrombolysis, antithrombosis and free radical scavenging, as well as the preparation method, composition, and applications thereof. The compound is represented by the formula I shown below:
(Continued)

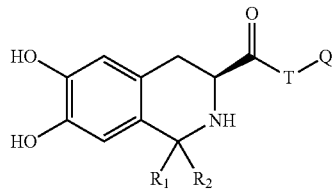

wherein the definitions of T, Q, $R_1$ and $R_2$ are described herein. The compound of the present invention simultaneously has triple functions of thrombolysis, free radical scavenging and thrombus-targeting/antithrombosis. The present invention also relates to a pharmaceutical composition comprising the compound, and a preparation method and a nanostructure of the compound.

6 Claims, 5 Drawing Sheets

(51) Int. Cl.
| | |
|---|---|
| C07D 217/00 | (2006.01) |
| C07K 5/097 | (2006.01) |
| C07K 5/02 | (2006.01) |
| C07K 5/11 | (2006.01) |
| C07K 5/078 | (2006.01) |
| A61K 47/54 | (2017.01) |
| A61K 47/55 | (2017.01) |
| A61K 38/00 | (2006.01) |

(52) U.S. Cl.
CPC .......... C07D 217/00 (2013.01); C07K 5/0215 (2013.01); C07K 5/06165 (2013.01); C07K 5/1019 (2013.01); *A61K 38/00* (2013.01)

(56) References Cited

U.S. PATENT DOCUMENTS

| | | | |
|---|---|---|---|
| 7,314,879 B2 | 1/2008 | Backer et al. | |
| 2015/0290339 A1* | 10/2015 | Peng | A61K 47/48246 424/489 |

FOREIGN PATENT DOCUMENTS

| | | | |
|---|---|---|---|
| CN | 101200493 A | 6/2008 | |
| CN | 101497651 A | 8/2009 | |
| CN | 101899084 A | 12/2010 | |
| CN | 102120727 A | 7/2011 | |
| CN | 102127097 A | 7/2011 | |
| CN | 102477068 A | 5/2012 | |
| CN | 102887941 A | 1/2013 | |
| CN | 103145797 A | 6/2013 | |
| CN | 103450330 A | 12/2013 | |
| CN | 103450338 A | 12/2013 | |
| WO | WO 2014/036821 | * 3/2013 | .............. C07K 7/06 |

OTHER PUBLICATIONS

Feng, Q. et al., "DHDMIQK(KAP): a novel nano-delivery system of dihydroxyl-tetrahydro-isoguinoline-3-carboxylic acid and KPAK towards the thrombus", Journal of Materials Chemistry B, Apr. 8, 2016, pp. 5991-6003.

* cited by examiner

SEQUENCE LISTING

```
<160> NUMBER OF SEQ ID NOS: 9

<210> SEQ ID NO 1
<211> LENGTH: 5
<212> TYPE: PRT
<213> ORGANISM: artificial sequence
<220> FEATURE:
<223> OTHER INFORMATION: synthesized

<400> SEQUENCE: 1

Ala Arg Pro Ala Lys
1               5

<210> SEQ ID NO 2
<211> LENGTH: 5
<212> TYPE: PRT
<213> ORGANISM: artificial sequence
<220> FEATURE:
<223> OTHER INFORMATION: synthesized
```

```
<400> SEQUENCE: 2

Gly Arg Pro Ala Lys
1               5

<210> SEQ ID NO 3
<211> LENGTH: 6
<212> TYPE: PRT
<213> ORGANISM: artificial sequence
<220> FEATURE:
<223> OTHER INFORMATION: synthesized

<400> SEQUENCE: 3

Gln Arg Arg Pro Ala Lys
1               5

<210> SEQ ID NO 4
<211> LENGTH: 4
<212> TYPE: PRT
<213> ORGANISM: artificial sequence
<220> FEATURE:
<223> OTHER INFORMATION: synthesized

<400> SEQUENCE: 4

Arg Pro Ala Lys
1

<210> SEQ ID NO 5
<211> LENGTH: 5
<212> TYPE: PRT
<213> ORGANISM: artificial sequence
<220> FEATURE:
<223> OTHER INFORMATION: synthesized

<400> SEQUENCE: 5

Gln Arg Pro Ala Lys
1               5

<210> SEQ ID NO 6
<211> LENGTH: 4
<212> TYPE: PRT
<213> ORGANISM: artificial sequence
<220> FEATURE:
<223> OTHER INFORMATION: synthesized

<400> SEQUENCE: 6

Lys Pro Ala Lys
1

<210> SEQ ID NO 7
<211> LENGTH: 4
<212> TYPE: PRT
<213> ORGANISM: artificial sequence
<220> FEATURE:
<223> OTHER INFORMATION: synthesized

<400> SEQUENCE: 7

Pro Ala Lys Pro
1

<210> SEQ ID NO 8
<211> LENGTH: 5
<212> TYPE: PRT
<213> ORGANISM: artificial sequence
<220> FEATURE:
<223> OTHER INFORMATION: synthesized
```

```
<400> SEQUENCE: 8

Ala Lys Pro Ala Lys
1               5

<210> SEQ ID NO 9
<211> LENGTH: 5
<212> TYPE: PRT
<213> ORGANISM: artificial sequence
<220> FEATURE:
<223> OTHER INFORMATION: synthesized

<400> SEQUENCE: 9

Pro Ala Lys Pro Ala
1               5
```

COMPOUNDS HAVING TRIPLE ACTIVITIES OF THROMBOLYSIS, ANTITHROMBOSIS, AND RADICAL SCAVENGING, SYNTHESIS, AND USE THEREOF

This application is a continuation of PCT/CN2014/079098, filed Jun. 3, 2014; which claims the priority of CN201310225330.6, filed Jun. 5, 2013. The contents of the above applications are incorporated herein by reference in their entireties.

TECHNICAL FIELD

The present invention relates to a novel compound simultaneously having thrombolytic, free radical scavenging and thrombus-targeting/antithrombotic functions as well as preparation method and uses thereof. The present invention further relates to a novel binary conjugate formed by coupling a thrombolytic oligopeptide and a tetrahydroisoquinoline compound having two $C_{1-4}$ alkyl groups via a linking arm. The present invention also relates to a pharmaceutical composition comprising the compound, a preparation method and a nanostructure of the compound.

BACKGROUND

The incidence rate of thrombotic diseases, such as stroke/infarction, ranks first in a variety of diseases. There is an increasing trend in the incidence rate of the diseases in recent years, and the diseases become a serious threat to human health. Drug treatment of the thrombotic diseases is the focus and hotspot of treating thrombosis. Currently, there are many limitations on clinically applied thrombotic drugs, and searching for a safe and effective new thrombus drug is one of the research hotspots.

According to present research, in addition to anti-platelet aggregation and anti-thrombotic activities, 3S-1, 1-dimethyl-6,7-dihydroxy-1,2,3,4-tetrahydro isoquinoline-3-carboxylic acid also has free radical scavenging activity. Moreover, in Chinese Patent Pubilication CN101497651 B, filed Jan. 30, 2008, 10 tetrahydroisoquinoline compounds having thrombolytic activity were disclosed. These tetrahydroisoquinoline compounds include 3S-6,7-1,2,3,4-tetrahydro-6,7-dihydroxy-isoquinoline-3-acyl-Pro-Ala-Lys, 3S-6,7-1,2,3,4-tetrahydro-6,7-dihydroxy-isoquinoline-3-acyl-Arg-Pro-Ala-Lys, 3S-6,7-1,2,3,4-tetrahydro-6,7-dihydroxy-isoquinoline-3-acyl-Ala-Arg-Pro-Ala-Lys, 3S-6,7-1,2,3,4-tetrahydro-6,7-dihydroxy-isoquinoline-3-acyl-Gly-Arg-Pro-Ala-Lys, 3S-6,7-1,2,3,4-tetrahydro-6,7-dihydroxy-isoquinoline-3-acyl-Gln-Arg-Pro-Ala-Lys, 3S-2-[Pro-Ala-Lys]-1,2,3,4-tetrahydro-6,7-dihydroxy-isoquinoline-3-carboxylic acid, 3S-2-[Arg-Pro-Ala-Lys]-1,2,3,4-tetrahydro-6,7-dihydroxy-isoquinoline-3-carboxylic acid, 3S-2-[Ala-Arg-Pro-Ala-Lys]-1,2,3,4-tetrahydro-6, 7-dihydroxy-isoquinoline-3-carboxylic acid, 3S-2-[Gly-Arg-Pro-Ala-Lys]-1,2,3,4-tetrahydro-6,7-dihydroxy-isoquinoline-3-carboxylic acid, and 3S-2-[Gln-Arg-Pro-Ala-Lys]-1,2,3,4-tetrahydro-6,7-dihydroxy-isoquinoline-3-carboxylic acid. The compounds above were abbreviated as "6,7-dihydroxy-isoquinolines having thrombolytic activity." However, the effective dosages of these 6,7-dihydroxy-isoquinolines having thrombolytic activity are higher, and the anti-thrombotic activity and the free radical scavenging activity were not disclosed or verified. Furthermore, the efficacy in treating stroke was demonstrated to be effective only at the time of stroke onset. As for treating stroke beyond 30 minutes from onset of syndrome, the efficacy was not disclosed or verified.

Therefore, for effectively and safely treating thrombotic diseases in clinical practice, a novel compound that simultaneously has thrombolytic, anti-thrombotic, and free radical scavenging activities, may effectively cross the blood-brain barrier (BBB), and may achieve the described effects at a low dose is needed.

SUMMARY

The first aspect of the present invention is to provide a compound having formula I:

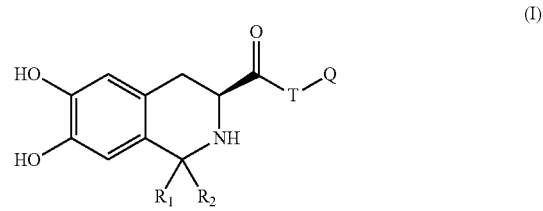

(I)

wherein T represents a linking arm having at least two groups for linking, Q represents a peptide having thrombolytic activity, $R_1$ and $R_2$ represents $C_{1-4}$ alkyl groups, wherein $R_1$ and $R_2$ may be the same or different.

In one embodiment of the present invention, at least one of the group for linking of the linking arm T is an amino group, and the remaining groups for linking are carboxyl group or amino group.

In a preferred embodiment of the present invention, the linking arm T may be a natural amino acid, such as L-Lys, L-Asp, or L-Glu.

In a more preferred embodiment of the present invention, the linking arm may be L-Lys.

In a preferred embodiment of the present invention, the peptide having thrombotic activity used in the present invention is selected from a group consisting of an oligopeptide having a PA (Pro-Ala) sequence, a PAK (Pro-Ala-Lys) sequence, a AKP (Ala-Lys-Pro) sequence or a KAP (Lys-Ala-Pro) sequence, and a peptide comprising repeated units of the PAK sequence, the AKP sequence or the KAP sequence.

In an embodiment of the present invention, the oligopeptide having thrombolytic activity may be a tripeptide to octapeptide containing a PA (Pro-Ala) sequence, a PAK sequence, a AKP sequence or a KAP sequence, preferably a tripeptide containing the PA sequence. In a more preferred embodiment, the tripeptide has a chemical formula of Q1 or Q2 shown below:

Pro-Ala-AA (Q1)

AA-Ala-Pro (Q2)

wherein AA is selected from a group consisting of L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu.

In a preferred embodiment, $R_1$ and $R_2$ both are methyl group.

In a preferred embodiment, the $R_1$ and $R_2$ of the formula I are methyl groups, the linking arm is L-Lys, L-Asp, or L-Glu, and the peptide having thrombolytic activity is a tripeptide containing a PA (Pro-Ala) sequence. For example, the compound may have the formula Ia (such as compound 5Aa-p in FIG. 1), Ib (such as compound 5Ba-p in FIG. 2), Ic (such as compound 5Ca-p in FIG. 3), Id (such as compound 5 Da-p in FIG. 4), Ie (such as compound 5Ea-p in FIG. 5), If (such as compound 5Fa-p in FIG. 6), Ig (such as compound 5Ga-p in FIG. 7), or Ih (such as compound 5Ha-p in FIG. 8):

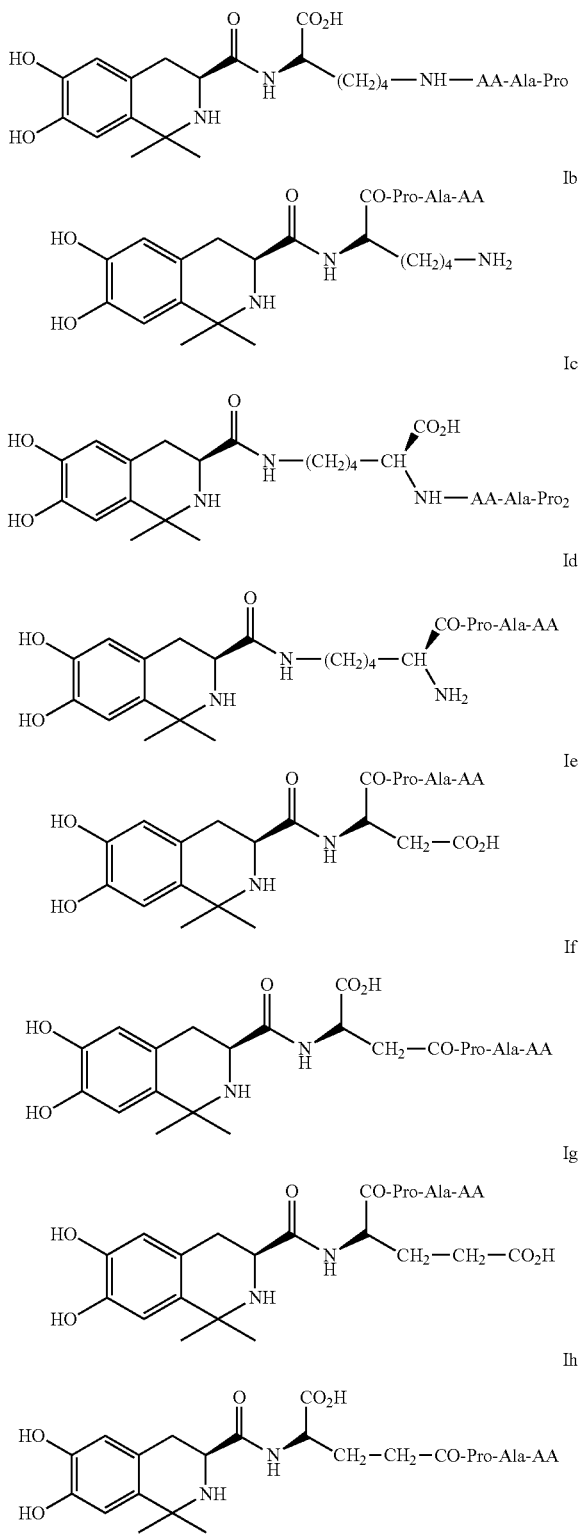

wherein AA is selected from a group consisting of L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu.

The second aspect of the present invention is to provide a pharmaceutical composition comprising the compound of the present invention described above and a pharmaceutically acceptable carrier.

In a preferred embodiment of the present invention, the compounds may be in the form of nanospherical structure.

In a preferred embodiment of the present invention, the pharmaceutical composition may be used as a thrombolytic drug, a NO free radical scavenging drug, or a thrombus-targeting/antithrombotic drug.

In another preferred embodiment of the present invention, the pharmaceutical composition may be used as a drug in treating stroke or cerebral infarction, more preferably, in treating stroke or cerebral infarction beyond 4 hours, 6 hours, and 24 hours from the onset of the syndrome, and treating via successive administration.

The third aspect of the present invention is to provide a preparation method of the compounds having formula I. The method comprises the following steps:

(1) provide a compound having formula II:

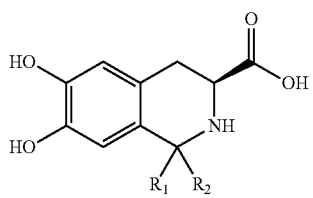

wherein R1 and R2 are C1-4 alkyl groups, and R1 and R2 are the same or different.

(2) providing the linking arm T having at least two groups for linking, and the peptide Q having thrombolytic activity, wherein the linking arm having a first group for linking and a second group for linking.

(3) coupling the carboxyl group of the compound having formula II with the first group for linking of the linking arm T to form a compound having formula IM-1:

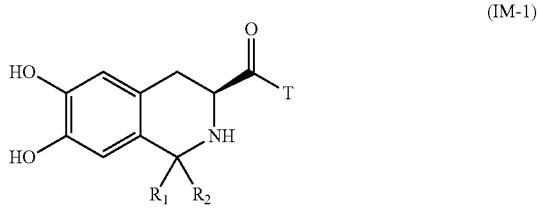

under appropriate reaction condition; and (4) coupling the peptide Q having thrombolytic activity with the compound having formula IM-1 under appropriate reaction condition, wherein one terminal of the peptide Q having thrombolytic activity is coupled to the second group for linking of the linking arm T to form the compound having formula I.

In an embodiment of the present invention, the first group for linking of the linking arm T is an amino group being used to couple to the carboxyl group of the compound of formula II in a condensation reaction. Moreover, the second group for linking is a carboxyl group or an amino group being used to couple to the N-terminal or C-terminal of the peptide Q having thrombolytic activity. The definitions of the linking arm T and the peptide Q having thrombolytic activity used in the preparation method of the invention are the same as the definitions of the compound having formula I above.

In a preferred embodiment of the present invention, the linking arm in the present preparation method may be L-Lys, L-Asp, or L-Glu, and more preferably L-Lys. The peptide having thrombolytic activity may be a tripeptide containing a PA (Pro-Ala) sequence, an oligopeptide containing a PAK (Pro-Ala-Lys) sequence, a AKP (Ala-Lys-Pro) sequence or a KAP (Lys-Ala-Pro) sequence, or a peptide having a repeated sequence containing the PAK sequence, the AKP sequencem or the KAP sequence, and more preferably a tripeptide having a formula of Q1 or Q2 shown below:

Pro-Ala-AA (Q1)

AA-Ala-Pro (Q2)

wherein AA is selected from a group consisting of L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu.

In another preferred embodiment of the present invention, the $R_1$ and $R_2$ of the compound having formula II both are methyl groups, the linking arm is L-Lys, L-Asp, or L-Glu, and the peptide having thrombolytic activity is a tripeptide containing a PA (Pro-Ala) sequence. In a more preferred embodiment of the present invention, the preparation method of the present invention may be used to form the compounds having the above formulas Ia-h.

The in vivo tests in rats showed that the compounds or the pharmaceutical compositions of the present invention have excellent thrombolytic and antithrombotic activities at low dose, and may effectively protect the neurological function of the stroke rats, thus may effectively and safely treat thrombotic diseases in clinical practice.

DETAILED DESCRIPTION

Figure 1:
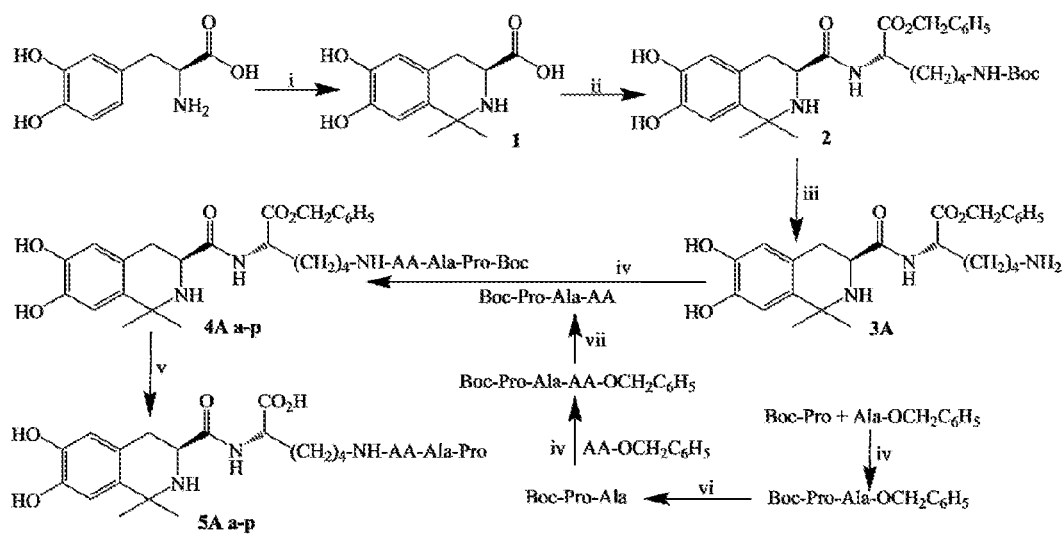
FIG. 1 is a synthesis scheme of compound Ia according to one embodiment of the present invention.

The detailed description provided below in connection with the appended drawings and embodiments is used to illustrate the technical solution of the present invention. However, the scopes of the present invention should be regarded as including but not limited thereto.

In the present invention, the tetrahydroiosquinoline compounds having two $C_{1-4}$ alkyl groups (i.e. the compound of formula II) and the peptide having thrombolytic activity are coupled via a linking arm to form a novel binary conjugate simultaneously having triple functions of thrombolytic, free radical scavenging, and thrombus-targeting/antithrombotic activities. The conjugate above is abbreviated as "the novel binary conjugate of the present invention" below.

Since two $C_{1-4}$ alkyl groups were introduced in position 1 and a linking arm was introduced in position 3 of the compound having formula II, "the novel binary conjugate of the present invention" has the following four advantages, as compared with "the 6,7-dihydroxyisoquinoline having thrombolytic activity." 1) The steric hindrance effect of the two $C_{1-4}$ alkyl groups introduced in position 1 of the compound having formula II may block the approach of the carboxypeptidase and the aminopeptidase, thus the thromobolytic oilgopeptide of "the novel binary conjugate of the present invention" will not be easily hydrolyzed; 2) the hydrophobic contribution of the two $C_{1-4}$ alkyl groups introduced in position 1 of the compound having formula II may allow "the novel binary conjugate of the present invention" to cross the blood-brain barrier with better efficiency; 3) the electron donating effect of the two $C_{1-4}$ alkyl groups introduced in the position 1 of the compound having formula II may allow the reducing ability of "the novel binary conjugate of the present invention" to satisfy the need for free radical scavenging; 4) the linking arm introduced in position 3 of the compound having formula II may allow "the novel binary conjugate of the present invention" to aggregate effectively together to form nanospherical structures having a diameter of 20-210 nm, preferably in a range of 20-100 nm. This stable nanostructure may assist "the novel binary conjugate of the present invention" in not being engulfed by macrophage in blood circulation, thus may be safely transported toward the thrombus forming site and finally cross the blood-brain barrier. In summary, "the novel binary conjugate of the present invention" may form a nanostructure to achieve the function of crossing blood-brain barrier. In addition to thrombolytic and antithrombotic functions, "the novel binary conjugate of the present invention" may also effectively scavenge the free radicals of OH, NO, and superoxide anions, and may achieve effective thrombolysis at low dose, thereby giving good prospects for clinical application.

As used herein, "group for linking" means a functional group, such as a carboxyl group or an amino group, capable of performing condensation reaction.

As used herein, "linking arm" means a molecule having the groups for linking, capable of coupling the compound having formula II with the oilgopeptide Q having thrombolytic activity. At least one group for linking of the linking arm is an amino group, and the remaining groups for linking are carboxyl groups or amino groups. According to the invention, the linking arm may be a natural amino acid, such as L-Lys, L-Asp, or L-Glu.

The introduced linking arm allows "the novel binary conjugate of the present invention" to form a stable nanospherical structure not being engulfed by macrophages. The nanospherical structure may be safely transported toward the thrombus forming site and finally cross the blood-brain barrier. Especially, when the linking arm is L-Lys, "the novel binary conjugate of the present invention" may effectively aggregate together to form nanospherical structures having a diameter of 20-210 nm, preferably in a range of 20-100 nm. The stable nanostructure may assist in preventing "the novel binary conjugate of the present invention" from being engulfed by macrophages in blood circulation, so as to enable its safe transportation toward the thrombus formation site and, finally, crossing the blood-brain barrier.

As used herein, an "oligopeptide" means a small peptide molecule having a molecular weight below 1000 Dalton (D) and usually consisting of 3 to 8 amino acids.

As used herein, a "peptide having thrombolytic activity" means an oligopeptide thrombolytic agent having functions of increasing vascular permeability and thrombolysis, including P6A (ARPAK) (SEQ ID NO: 1), metabolites of P6A, and related derivatives. A previous study has disclosed that Pro-Ala-Lys was the shortest sequence with good activity, and also the stablest sequence among several thromobolytic oilgopeptides, including Ala-Arg-Pro-Ala-Lys (SEQ ID NO: 1), Gly-Arg-Pro-Ala-Lys (SEQ ID NO: 2), Gln-Arg-Arg-Pro-Ala-Lys (SEQ ID NO: 3) and Pro-Ala-Lys. Introducing a tripeptide having Pro-Ala-AA sequence to the position 3 of the compound having formula II via the linking arm may allow "the novel binary conjugate of the present invention" to obtain better stability and stronger thrombolytic activity.

For example, an oligopeptide containing the sequence of PAK, AKP, or KAP used in the present invention may be PAK, RPAK(Arg-Pro-Ala-Lys) (SEQ ID NO: 4), ARPAK (Ala-Arg-Pro-Ala-Lys) (SEQ ID NO: 1), GRPAK (Gly-Arg-Pro-Ala-Lys) (SEQ ID NO: 2), QRPAK (Gln-Arg-Pro-Ala-Lys) (SEQ ID NO: 5), AKP, KAP, KPAK (Lys-Pro-Ala-Lys) (SEQ ID NO: 6), PAKP (Pro-Ala-Lys-Pro) (SEQ ID NO: 7), AKPAK (Ala-Lys-Pro-Ala-Lys) (SEQ ID NO: 8), or PAKPA (Pro-Ala-Lys-Pro-Ala) (SEQ ID NO: 9).

For example, the peptide having repeating units of the PAK sequence, the AKP sequence or the KAP sequence used in the present invention may be any of those peptides being described in the Chinese patent publication CN101190941 as a peptide having thrombolytic activity, including a peptide having repeating units of the PAK sequence, such as $(PAK)_2$, $(PAK)_3$, $(PAK)_4$, $(PAK)_5$ and $(PAK)_6$; a peptide having repeating units of the AKP sequence, such as $(AKP)_2$, $(AKP)_3$, $(AKP)_4$, $(AKP)_5$ and $(AKP)_6$; and a peptide having repeating units of the KPA sequence, such as $(KPA)_2$, $(KPA)_3$, $(KPA)_4$, $(KPA)_5$ and $(KPA)_6$.

As used herein, "$C_{1-4}$ alkyl group" means an alkyl group having 1-4 carbons, such as methyl, ethyl, n-propyl, isopropyl, butyl, isobutyl, or sec-butyl, tert-butyl. When $R_1$ and $R_2$ of the compound having formula I both are methyl groups, the compound having formula II, used as a starting material, may be obtained by Pictet-Spengler condnesation of 3,4-dihydroxy-L-phenylalanine and acetone in the presense of trifluoroacetate (TFA) and anhydrous magnesium sulfate. The advantage is easier preparation.

In the present invention, a pharmaceutical composition may be any clinically acceptable and suitable formulations. Preferably, the formulation is injectable formulations (powder for injection, lyophilized powder for injection, liquid for injection, infusion, etc.). The pharmaceutically acceptable carrier may be mannitol, water, Ringer's solution, or isotonic sodium chloride solution, etc.

The nanospherical structure of the compounds according to the present invention has a diameter of 20-210 nm, and more preferably, 20-100 nm, by which the compounds may cross the blood-brain barrier more efficiently.

The stable nanostructure may help the compounds of the present invention not to be engulfed by macrophages, by which the compounds may be safely transported toward the thrombosis formation site and eventually cross the blood-brain barrier. The pharmaceutical composition of the present invention may be used as a thrombolytic drugs in treating myocardial infarction, ischemic stroke, deep vein thrombosis, pulmonary embolism, peripheral arterial occlusive disease, occluded central vascular access devices, clotted arteriovenous fistula and shunts, carotid stenosis, etc. The pharmaceutical composition of this invention may also be used as a NO free radical scavenging drug in treating neurodegenerative diseases, cardiovascular disease, mental illness, altitude sickness, diabetes, rheumatoid arthritis, traumatic brain injury, cancer, fragile x syndrome, sickle cell disease, lichen planus, vitiligo, chronic fatigue syndrome, etc. The pharmaceutical composition of the present invention may also be used as a thrombus-targeting/antithrombotic drug in treating thrombocytosis, myeloproliferative disease, polycythemia vera, budd-chiari syndrome, etc.

The pharmaceutical compositions/compounds of the present invention simultaneously have OH, NO and superoxide anionic free radical scavenging, thrombolytic, as well as thrombus-targeting/antithrombotic functions. Accordingly, they may remain therapeutically effective in patients beyond 4 hours from the onset of stroke symptoms, i.e. their use is not limited by the 3-hour treatment window of tPA. Moreover, the use of the pharmaceutical compositions/compounds of the present invention will not cause systemic bleeding reactions as tPA does, and may scavenge the massive amount of free radicals of OH, NO, and superoxide anions during the ischemia-reperfusion process so as to prevent brain tissue damages for patients being treated. Since the two $C_{1-4}$ alkyl groups and the linking arm are respectively introduced in the positions 1 and 3 of the compounds having formula II, as compared with "the 6,7-dihydroxyisoquinoline having thrombolytic activity," "the novel binary conjugate of the present invention" shows better thrombolytic activity, unique free radical scavenging and antithrombotic activity at a low dose, as well as excellent therapeutic effect in treating stroke beyond 4 hours from the stroke onset at a higher dose.

In the issued Chinese Patent, No. CN101497651B, "the 6,7-dihydroxyisoquinoline having thrombolytic activity" was shown to have thrombolytic activity at a dose of 10 nmol/kg. However, the compounds of the present invention have good thrombolytic and antithrombotic activity at a dose of 0.1 nmol/kg. Moreover, the compounds of the present invention have significant therapeutic effect in treating stroke beyond 4, 6, and 24 hours from the stroke onset at a dose of 1, 2.5, and 5 μmol/kg, respectively.

In the preparation method of the compounds of the present invention, the peptide Q having thrombolytic activity may be prepared first and then coupled to the second group for linking of the linking arm T, alternatively, one or more of the amino acids of the peptide Q having thrombolytic activity may be sequentially coupled to the linking arm T in a predetermined order. For example, the first amino acid at one terminal of the thrombolytic peptide Q is coupled to the second group for linking of the linking arm T, and one or more of the rest of the amino acids are then sequentially coupled thereto.

The preparation method of the present invention is described in more detail below for further understanding.

The compound of formula II may be prepared by the following synthesis route:

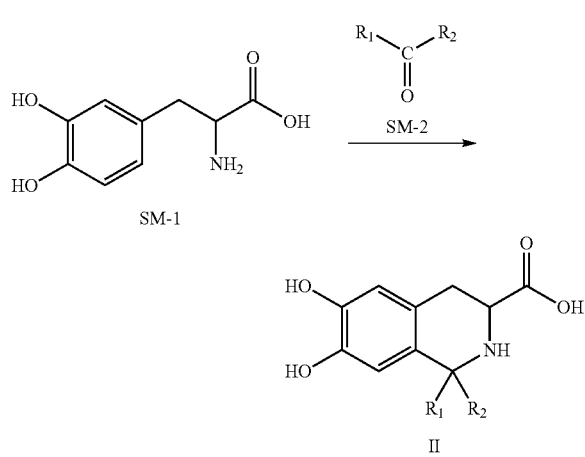

wherein $R_1$ and $R_2$ both are $C_{1-4}$ alkyl group and may be the same or different. For example, 3,4-dihydroxy-L-phenylalanine (SM-1) and the compound SM-2 are dissolved in TFA, and the 3,4-dihydroxy-L-phenylalanine and SM-2 undergo Pictet-Spengler condensation to obtain the compound having formula II in the presence of anhydrous magnesium sulfate.

In a preferred embodiment, the linking arm in the preparation method of the invention is L-Lys, and the peptide having thrombolytic activity is a tripeptide having a sequence of PA (Pro-Ala). For example, the carboxyl group of the compound II is coupled to a N-terminal of the L-Lys, and then the tripeptide containing the PA sequence is coupled to the rest N-terminal or the C-terminal of the L-Lys linking arm. In some embodiments, when the $R_1$ and $R_2$ both are methyl group (i.e. 3S-6,7-dihydroxy-1,1-dimethyl-1,2,3,4-tetrahydro-isoquinoline-3-acyl-carboxylic acid), the linking arm is L-Lys, and the peptide having thrombolytic activity is the tripeptide containing the PA (Pro-Ala) sequence, the compound Ia, Ib, Ic, or Id may be obtained according to the preparation method of the present invention.

When the compound Ia is prepared according to the preparation method of the present invention, the synthesis route disclosed in FIG. 1 may be referred.

In the embodiment shown in FIG. 1, the tripeptide containing the PA sequence is synthesized first and then coupled to the L-Lys linking arm, wherein the AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5Aa-p,). The reaction conditions are listed below: i) Acetone, TFA, MgSO₄; ii) HCl, Lys(Boc)-OBzl, DCC, HOBt, NMM; iii) 4M HCl/EA, ice bath; iv) DCC, HOBt, NMM, v) EtOH, Pd/C; 4M HCl/EA, ice bath; vi) EtOH, Pd/C; vii) 2M NaOH. In another embodiment, one amino acid of the tripeptide containing the PA sequence (such as AA) is coupled to the L-Lys linking arm, and the rest two amino acids (such as Pro-Ala) of the tripeptide containing the PA sequence are then coupled to AA.

For example, in an embodiment of forming compound Ia, the preparation method of the present invention may include the following steps:

1) In the presence of TFA and anhydous magnesium sulfate, making 3,4-dihydroxy-L-phenylalanine and acetone undergo Pictet-Spengler condensation to obtain 3S-6,7-dihydroxy-1,1-dimethyl-1,2,3,4-tetrahydro-isoquinoline-3-acyl-carboxylic acid;

2) In the presence of dicyclohexyl carbodiimide (DCC) and N-hydroxybenzotriazole triazole (HOBt), condensing the 3S-6,7-dihydroxy-1,1-dimethyl-1,2,3,4-tetrahydro-isoquinoline-3-acyl-carboxylic acid and HCl.Lys(Boc)-OBzl, in anhydrous N,N-dimethylformamide (DMF), to form 3S-6,7-dihydroxy-1,1-dimethyl-1,2,3,4-tetrahydroisoquinoline-3-acyl-Lys(Boc)-Obzl. In the condensation reaction, N-methylmorpholine (NMM) was used to constantly adjust the mixture to pH=9;

3) Removing Boc from the 3S-6,7-dihydroxy-1,1-dimethyl-1,2,3,4-tetrahydroisoquinoline-3-acyl-Lys(Boc)-OBzl in a ethyl acetate solution of HCl to obtain 3S-6,7-dihydroxy-1,1-dimethyl-1,2,3,4-tetrahydroisoquinoline-3-acyl-Lys-OBzl;

4) In the presence of DCC and HOBt, condensing Boc-Pro with Tos.Ala-Obzl, in anhydrous THF, to form Boc-Pro-Ala-OBzl;

5) In EtOH, hydrogenolyzing the Boc-Pro-Ala-OBzl to form Boc-Pro-Ala;

6) In the presence of DCC and HOBt, condensing the Boc-Pro-Ala with AA-Obzl, in anhydrous THF, to form Boc-Pro-Ala-AA-OBzl (AA is selected from L-Ala, Gly, L-Phe, L-Val, L-Leu, L-Ile, L-Trp, L-Ser, L-Thr, L-Tyr, L-Lys(Z), L-Pro, L-Asn, and L-Gln residues);

7) In EtOH, hydrogenolyzing the Boc-Pro-Ala-AA-OBzl of step 6 to form Boc-Pro-Ala-AA;

8) In the presence of DCC and HOBt, condensing the 3S-6,7-dihydroxy-1,1-dimethyl-1,2,3,4-tetrahydroisoquinoline-3-acyl-Lys-OBzl with the Boc-Pro-Ala-AA of step 6, in anhydrous DMF, to form 3S-6,7-dihydroxy-1,1-dimethyl-1,2,3,4-tetrahydroisoquinoline-3-acyl-Lys(Boc-Pro-Ala-AA)-OBzl (the definition of AA is the same as that in step 6);

9) In the presence of DCC and HOBt, condensing the 3S-6,7-dihydroxy-1,1-dimethyl-1,2,3,4-tetrahydroisoquinoline-3-acyl-Lys-OBzl with Boc-AA(OBzl), in anhydrous DMF, to form 3S-6,7-dihydroxy-1,1-dimethyl-1,2,3,4-tetrahydroisoquinoline-3-acyl-Lys[Boc-AA(OBzl)]-OBzl (AA is selected from L-Asp, L-Glu residues);

10) In ethyl acetate solution of HCl, removing Boc from the 3S-6,7-dihydroxy-1,1-dimethyl-1,2,3,4-tetrahydroisoquinoline-3-acyl-Lys[Boc-AA (OBzl)]-OBzl to form 3S-6,7-dihydroxy-1,1-dimethyl-1,2,3,4-tetrahydro isoquinoline-3-acyl-Lys[AA(OBzl)]-OBzl (the definition of AA is the same as that in step 9);

11) In the presence of DCC and HOBt, condensing the 3S-6,7-dihydroxy-1,1-dimethyl-1,2,3,4-tetrahydroisoquinoline-3-acyl-Lys [AA(OBzl)]-OBzl with Boc-Pro-Ala, in anhydrous DMF, to form 3S-6,7-dihydroxy-1,1-dimethyl-1,2,3,4-tetrahydroisoquinoline-3-acyl-Lys[Boc-Pro-Ala-AA (OBzl)]-OBzl (the definition of AA is the same as that in step 9);

12) By hydrogenolysis and the removal of Boc, deprotecting the both 3S-6,7-dihydroxy-1,1-dimethyl-1,2,3,4-tetrahydroisoquinoline-3-acyl-Lys(Boc-Pro-Ala-AA)-OBzl (the definition of AA is the same as that in step 6) and the 3S-6,7-dihydroxy-1,1-dimethyl-1,2,3,4-tetrahydroisoquinoline-3-acyl-Lys[Boc-Pro-Ala-AA(OBzl)]-OBzl (the definition of AA is the same as that in step 9) to obtain 3S-6,7-dihydroxy-1,1-dimethyl-1,2,3,4-tetrahydroisoquinoline-3-acyl-Lys (Pro-Ala-AA).

Figure 2:
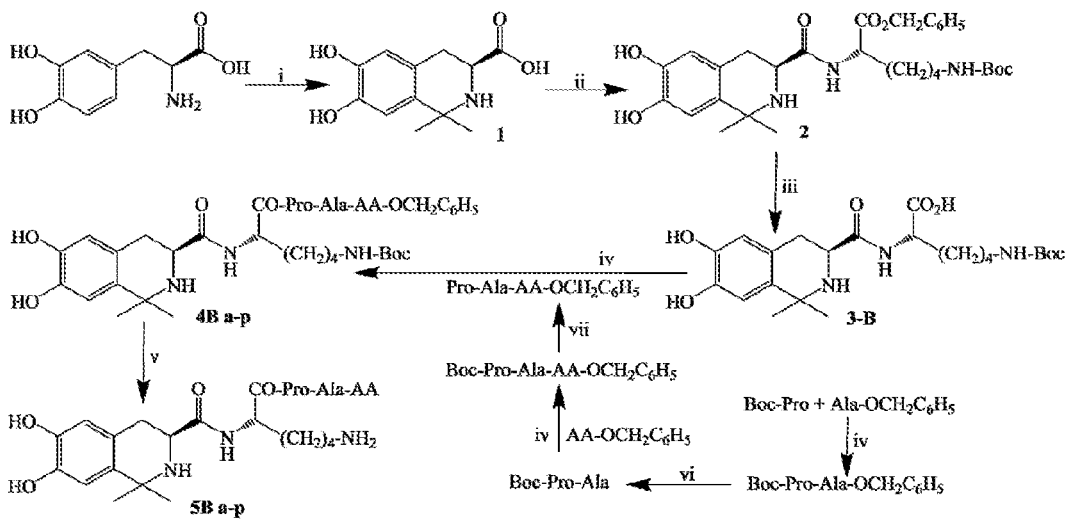
FIG. 2 is a synthesis scheme of compound Ib according to one embodiment of the present invention.

When compound Ib of the present invention is prepared according to the preparation method of the present invention, synthesis route shown in FIG. 2 may be referred, wherein AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5Ba-p). The reaction conditions are listed below: i) Acetone, TFA, MgSO4; ii) HCl, Lys(Boc)-OBzl, DCC, HOBt, NMM; iii) EtOH, Pd/C; iv) DCC, HOBt, NMM, v) EtOH, Pd/C; 4M HCl/EA, ice bath; vi) EtOH, Pd/C; vii) 4M HCl/EA, ice bath.

Figure 3:
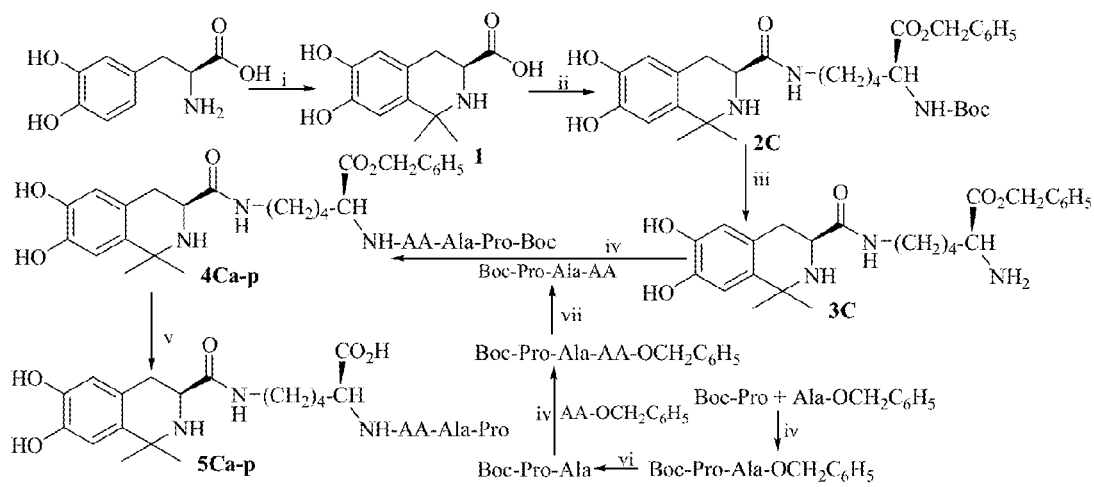
FIG. 3 is a synthesis scheme of compound Ic according to one embodiment of the present invention.

When compound Ic of the present invention is prepared according to the preparation method of the present invention, synthesis route shown in FIG. 3 may be referred, wherein AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5Ca-p). The reaction conditions are listed below: i) Acetone, TFA, MgSO$_4$; ii) HCl, Boc-Lys-OBzl, DCC, HOBt, NMM; iii) 4M HCl/EAice bath; iv) DCC, HOBt, NMM, v) EtOH, Pd/C; 4M HCl/EA, ice bath; vi) EtOH, Pd/C; vii) EtOH, Pd/C.

Figure 4:
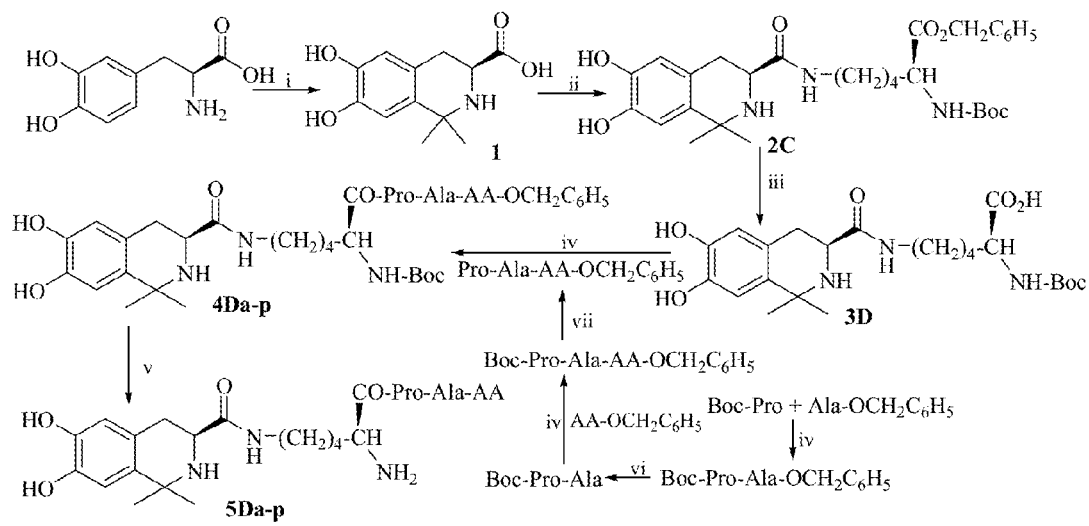
FIG. 4 is a synthesis scheme of compound Id according to one embodiment of the present invention.

When compound Id of the present invention is prepared according to the preparation method of the present invention, synthesis route shown in FIG. 4 may be referred, wherein AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5 Da-p). The reaction conditions are listed below: i) Acetone, TFA, MgSO$_4$; ii) HCl, Boc-Lys-OBzl, DCC, HOBt, NMM; iii) EtOH, Pd/C; iv) DCC, HOBt, NMM, v) EtOH, Pd/C; 4M HCl/EA, ice bath; vi) EtOH, Pd/C; vii) EtOH, Pd/C.

In another preferred embodiment, the linking arm is L-Asp, and the peptide having thrombolytic activity is a tripeptide containing a PA (Pro-Ala) sequence. For example, the carboxyl group of the compound having formula II is coupled to the N-terminal of L-Asp, and then the tripeptide containing the PA sequence is coupled to one of the rest C-terminal of the L-Asp linking arm. In some embodiments, when the $R_1$ and $R_2$ of the compound having formula II both are methyl group (i.e. 3S-6,7-dihydroxy-1,1-dimethyl-1,2,3,4-tetrahydro-isoquinoline-3-acyl-carboxylic acid), the linking arm is L-Asp, and the peptide having thrombolytic activity is the tripeptide containing the PA (Pro-Ala) sequence, the preparation method of the present invention may form the compounds Ie or If above.

Figure 5:
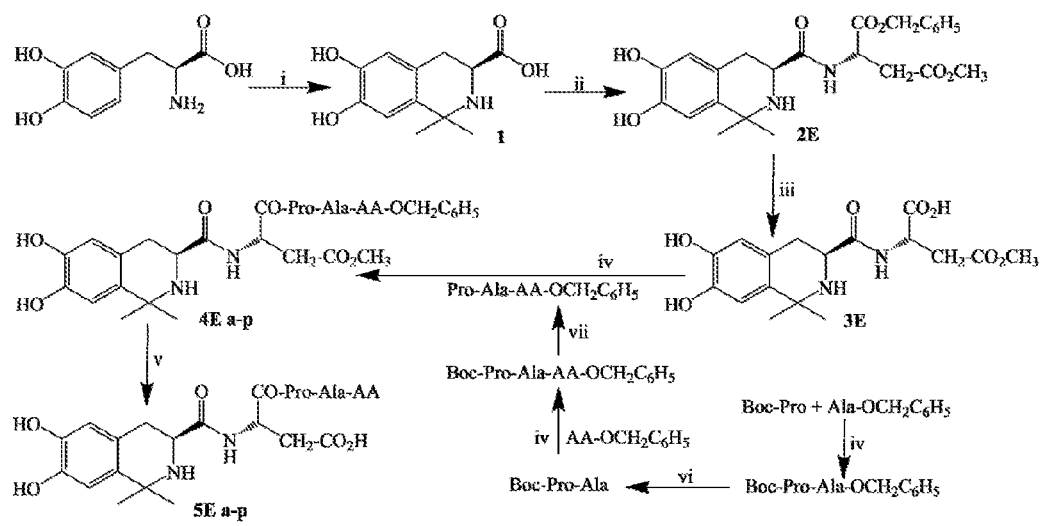
FIG. 5 is a synthesis scheme of compound Ie according to one embodiment of the present invention.

When compound Ie of the present invention is prepared according to the preparation method of the present invention, synthesis route shown in FIG. 5 may be referred, wherein AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5Ea-p). The reaction conditions are listed below: i) Acetone, TFA, MgSO4; ii) HCl, Asp(OCH$_3$)—OBzl, DCC, HOBt, NMM; iii) EtOH, Pd/C; iv) DCC, HOBt, NMM, v) EtOH, Pd/C; 2M NaOH, ice bath; vi) EtOH, Pd/C; vii) 4M HCl/EA, ice bath.

Figure 6:
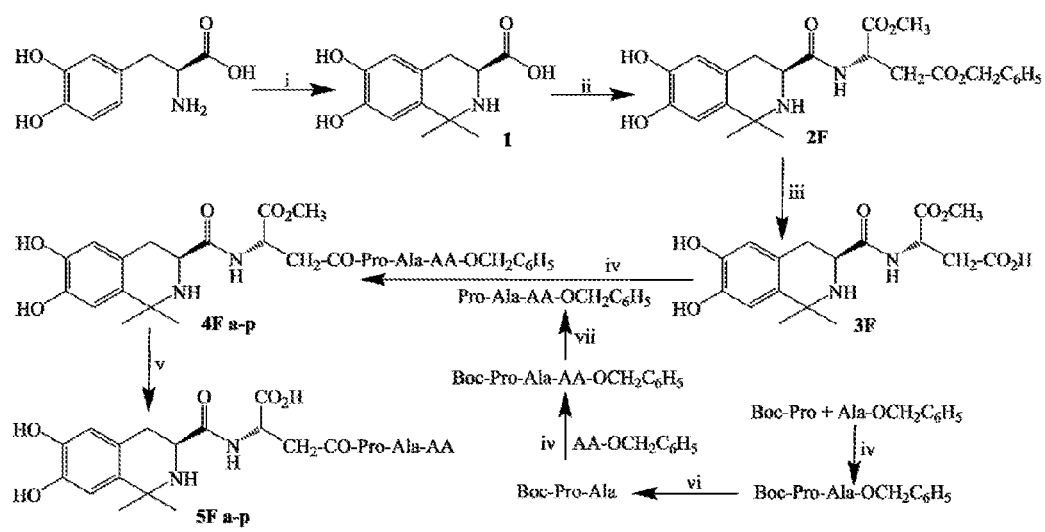
FIG. 6 is a synthesis scheme of compound If according to one embodiment of the present invention.

When compound If of the present invention is prepared according to the preparation method of the present invention, synthesis route shown in FIG. 6 may be referred, wherein AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5Fa-p). The reaction conditions are listed below: i) Acetone, TFA, MgSO4; ii) HCl, Asp(OBzl)-OCH$_3$, DCC, HOBt, NMM; iii) 2M NaOH, iv) DCC, HOBt, NMM, v) EtOH, Pd/C; 2M NaOH, ice bath; vi) EtOH, Pd/C; vii) 4M HCl/EA, ice bath.

In another preferred embodiment of the present invention, the linking arm is L-Glu, and the peptide having thrombolytic activity is a tripeptide containing a PA (Pro-Ala) sequence. For example, the carboxyl group of the compound having formula II is coupled to the N-terminal of L-Glu, and then the tripeptide containing the PA sequence is coupled to one of the rest C-terminal of the linking arm L-Glu. In some embodiments, when the $R_1$ and $R_2$ of the compound having formula II both are methyl groups (i.e. 3S-6,7-dihydroxy-1,1-dimethyl-1,2,3,4-tetrahydro-isoquinoline-3-acyl-carboxylic acid), the linking arm is L-Glu, and the peptide having thrombolytic activity is the tripeptide containing the PA (Pro-Ala) sequence, the preparation method of the present invention may form the compounds Ig or Ih above.

Figure 7:
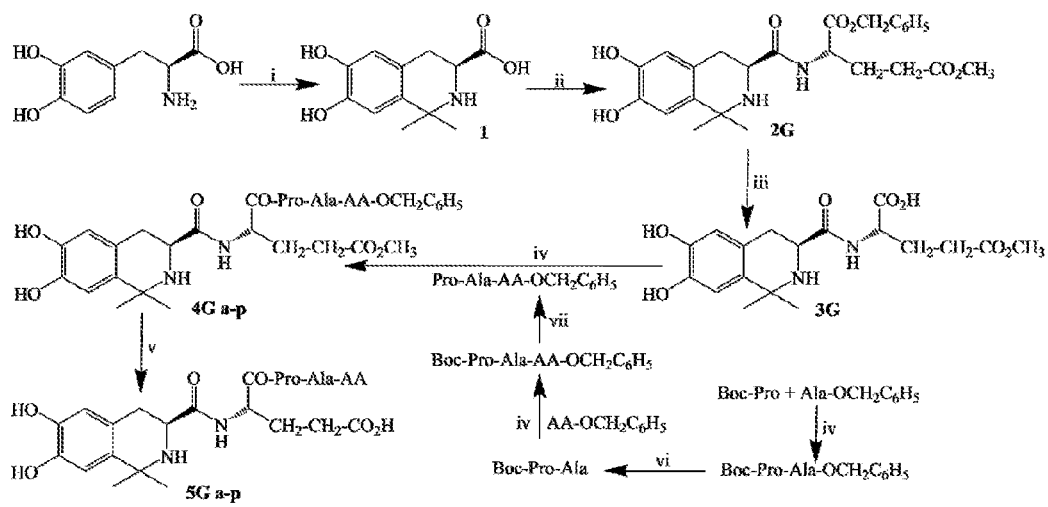
FIG. 7 is a synthesis scheme of compound Ig according to one embodiment of the present invention.

When compound Ig of the present invention is prepared according to the preparation method of the present invention, synthesis route shown in FIG. 7 may be referred, wherein AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5Ga-p). The reaction conditions are listed below: i) Acetone, TFA, MgSO4; ii) HCl, Glu(OCH$_3$)—OBzl, DCC, HOBt, NMM; iii) EtOH, Pd/C; iv) DCC, HOBt, NMM; v) EtOH, Pd/C; 2M NaOH, ice bath; vi) EtOH, Pd/C; vii) 4M HCl/EA, ice bath.

Figure 8:
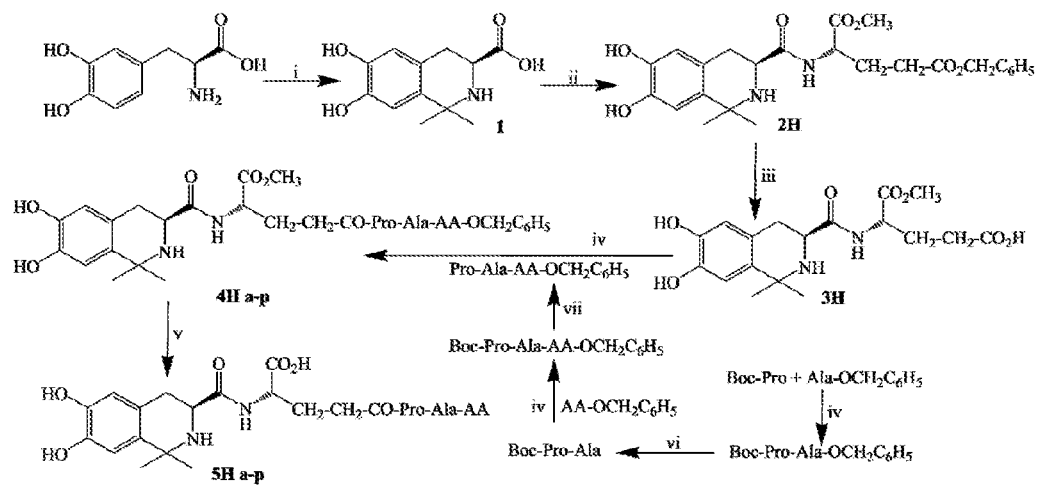
FIG. 8 is a synthesis scheme of compound Ih according to one embodiment of the present invention.

When compound Ih of the present invention is prepared according to the preparation method of the present invention, synthesis route shown in FIG. 8 may be referred, wherein AA is selected from L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu residue (respectively corresponding to compounds 5Ha-p). The reaction conditions are listed below: i) Acetone, TFA, MgSO4; ii) HCl, Glu(O Bzl)-OCH$_3$, DCC, HOBt, NMM; iii) EtOH, Pd/C; iv) DCC, HOBt, NMM; v) EtOH, Pd/C; 2M NaOH, ice bath; vi) EtOH, Pd/C; vii) 4M HCl/EA, ice bath.

The in vivo tests in rats of the compounds and pharmaceutical compostions of the present invention show that the compounds and pharmaceutical compostions of the present invention have excellent thrombolytic and antithombotic activity at low dose, and may effectively protect the neurological functions of the stroke rats. Therefore, the compounds and pharmaceutical compostions of the present invention may effectively and safely treat thrombotic diseases in clinical practice.

The present invention will now be described in connection with the following specific examples, and the advantages and features thereof will become apparent in view of the description. These examples are merely illustrative and in no way limit the scope of the present invention. A person skilled in the art can understand that modification or substitution may be made in details and formality of the technical solutions of the present invention without deviating from the spirit and scope of the present invention, and these modifications or substitutions are intended to be within the scope of protection of the present invention.

Examples 1-68 illustrate the preparation methods in FIG. 1 for preparing compounds 5Aa-p of the present invention.

Example 1: General Procedure for Synthesizing Peptide in Liquid Phase

An amino acid having a protected N-terminal was dissolved in anhydrous tetrahydrofuran (THF), and the obtained solution was added with N-hydroxybenzotriazole triazole (HOBt). Ice bath the solution. N, N-dicyclohexyl carbodiimide (DCC) dissolved in anhydrous THF was slowly added thereto, and then stirred at 0° C. for 15 minutes to obtain the reaction solution (I). An amino acid having a protected C-terminal was also dissolved in anhydrous THF while adjusted to pH 9 by N-methylmorpholine (NMM), and then mixed with the reaction solution (I) while maintained at pH9 by N-methylmorpholine (NMM). The reaction mixture was stirred at room temperature for 10 hours, and the reaction progress was monitored by TLC. Until the starting material spot disappeared as shown by TLC, the reaction mixture was filtered and the filtrate was concentrated under reduced pressure. The obtained viscous concentrate was dissolved by ethyl acetate (EA) or dichloromethane, the obtained solution was sequentially washed by 5% NaHCO$_3$ aqueous solution, 5% KHSO$_4$ aqueous solution, and saturated NaCl aqueous solution. The EA or dichloromethane phase was dried by anhydrous magnesium sulfate, filtered, and the filtrate was concentrated under a reduced pressure to obtain the target compound.

Example 2: General Procedure for Removing Boc

Boc protected peptide was dissolved by a small amount of anhydrous ethyl acetate, ethyl acetate solution of HCl (4 M) was added thereto and stirred on an ice bath until the starting material spot disappeared as shown by TLC. The reaction solution was repeatedly dried by a water pump, and HCl gas was also removed completely. The residue was triturated with petroleum ether or anhydrous ether repeatedly to obtain the target compounds.

Example 3: General Procedure for Removing Benzyl Ester Group

Benzyl ester group protected polypeptide was dissolved by CH$_3$OH, NaOH aqueous solution (2M) was dropwise added thereto and stirred on an ice bath, the reaction solution was maintained at 0° C. until the starting material spot disappeared as shown by TLC. The reaction solution was adjusted to neutral with 1 M HCl, and removed MeOH by reduced pressure. The reaction solution was acidified to pH 2 with 1 M HCl and then extracted by EA. The combined EA phase was washed by saturated NaCl aqueous solution to neutral, dried by anhydrous Na$_2$SO$_4$, and filtered. The filtrate was concentrated under reduced pressure to obtain the target compounds.

Example 4: General Procedure for Removing Carbobenzoxy Group or Benzyl Ester Group Carbobenzoxy group or benzyl ester group protected peptide was dissolved in suitable amount of EtOH, Pd/C (10% of reactants) was added thereto, and hydrogen was introduced to perform hydorgenolysis reaction at room temperature. After reaction, the reaction mixture was filtered and then concentrated under reduced pressure to obtain the target compound.

Example 5: Preparation of Boc-Pro 5.75 g (50 mmol) L-Pro was dissolved in 1 mL water. 25 mL NaOH aqueous solution (2M) was dropwise added thereto and stirred slowly on an ice bath to obtain solution (I). 13.08 g (60 mmol) (Boc)$_2$O was dissolved in 25 mL dioxane to obtain solution (II). Solution (II) was dropwise added to solution (I) and stirred on an ice bath, and then NaOH aqueous solution (2M) was dropwise added to adjust pH 9, and the mixture was stirred on an ice bath. After 30 minutes, pH value of the mixture was measured, and NaOH aqueous solution (2M) was used to maintain pH value at 9. Water pump was used to extract the generated gas. After stirring for 48 hours, the TLC monitoring (CH$_2$Cl$_2$: MeOH 20:1) showed that the reaction was completed. The mixture was concentrated under a reduced pressure to remove dioxane. The residue was dissolved by 5 mL water, and then adjust to pH 2 by saturated KHSO$_4$ aqueous solution. The aqueous solution was extracted by EA for 3 times. Combined EA phase was washed by 5% KHSO$_4$ for 3 times, and then washed by saturated NaCl aqueous solution to neutral. The separated EA layer was dried by adding anhydrous sodium sulfate and then filtered. The filtrate was concentrated under reduced pressure. The residue was recrystallized by EA-petroleum ether to obtain 10.2 g (95%) of the title compound as a colorless crystal. ESI-MS (m/e): 214 [M−H].

Example 6: Preparation of Boc-Pro-Ala-OBzl

By following the method of Example 1, 5.19 g (68%) of the title compound as colorless powder was prepared from 4.3 g (20.0 mmol) Boc-Pro and 8.45 g (24.0 mmol) Tos.Ala-OBzl. ESI-MS (m/e): 377 [M+H]$^+$.

Example 7: Preparation of Boc-Pro-Ala

By following the method of Example 4, 3.59 g (91%) of the title compound as colorless powder was prepared from 5.19 g (13.8 mmol) Boc-Pro-Ala-OBzl. ESI-MS (m/e): 285 [M−H]$^-$.

Example 8: Preparation of Boc-Pro-Ala-Ala-OBzl

By following the method of Example 1, 3.04 g (68%) of the title compound as colorless powder was prepared from 3.00 g (10.49 mmol) Boc-Pro-Ala-OBzl and 3.26 g (12.03 mmol) Tos.Ala-OBzl. ESI-MS (m/e): 448 [M+H]$^+$.

Example 9: Preparation of Boc-Pro-Ala-Ala

By following the method of Example 3, 3.21 g (90%) of the title compound was prepared from 4.47 g (10 mmol) Boc-Pro-Ala-Ala-OBzl. ESI-MS (m/e): 356 [M−H]$^-$.

Example 10: Preparation of Boc-Pro-Ala-Val-OBzl

By following the method of Example 1, 3.28 g (69%) of the title compound as colorless powder was prepared from 3.00 g (10.49 mmol) Boc-Pro-Ala and 3.58 g (12.01 mmol) Tos.Val-OBzl. ESI-MS (m/e): 476 [M+H]$^+$.

Example 11: Preparation of Boc-Pro-Ala-Val

By following the method of Example 3, 3.54 g (92%) of the title compound was prepared from 4.75 g (10 mmol) Boc-Pro-Ala-Val-OBzl. ESI-MS (m/e): 384 [M−H]$^-$.

Example 12: Preparation of Boc-Pro-Ala-Trp-OBzl

By following the method of Example 1, 3.65 g (65%) of the title compound as colorless powder was prepared from 3.00 g (10.49 mmol) Boc-Pro-Ala and 3.97 g (12.01 mmol) HCl.Trp-OBzl. ESI-MS (m/e): 563 [M+H]$^+$.

Example 13: Preparation of Boc-Pro-Ala-Trp

By following the method of Example 3, 4.21 g (89%) of the title compound was prepared from 5.62 g (10 mmol) Boc-Pro-Ala-Trp-OBzl. ESI-MS (m/e): 471 [M−H]$^-$.

Example 14: Preparation of Boc-Pro-Ala-Tyr-OBzl

By following the method of Example 1, 3.73 g (69%) of the title compound as colorless powder was prepared from 3.15 g (11 mmol) Boc-Pro-Ala and 4.43 g (10 mmol) Tos.Tyr-OBzl. ESI-MS (m/e): 540 [M+H]$^+$.

Example 15: Preparation of Boc-Pro-Ala-Tyr

By following the method of Example 3, 4.13 g (92%) of the title compound was prepared from 5.39 g (10 mmol) Boc-Pro-Ala-Tyr-OBzl. ESI-MS (m/e): 448 [M−H]$^-$.

Example 16: Preparation of Boc-Pro-Ala-Phe-OBzl

By following the method of Example 1, 3.82 g (66%) of the title compound as colorless powder was prepared from 3.00 g (10.0 mmol) Boc-Pro-Ala and 2.92 g (11.0 mmol) Tos.Phe-OBzl. ESI-MS (m/e): 524 [M+H]$^+$.

Example 17: Preparation of Boc-Pro-Ala-Phe

By following the method of Example 3, 3.94 g (91%) of the title compound was prepared from 5.23 g (10 mmol) Boc-Pro-Ala-Phe-OBzl. ESI-MS (m/e): 432 [M−H]$^-$.

Example 18: Preparation of Boc-Pro-Ala-Gly-OBzl

By following the method of Example 1, 2.90 g (67%) of the title compound as colorless powder was prepared from 3.15 g (11 mmol) Boc-Pro-Ala and 3.37 g (10 mmol) Tos.Gly-OBzl. ESI-MS (m/e): 434 [M+H]$^+$.

Example 19: Preparation of Boc-Pro-Ala-Gly

By following the method of Example 3, 2.98 g (87%) title compound was prepared from 4.33 g (10 mmol) Boc-Pro-Ala-Gly-OBzl. ESI-MS (m/e): 342 [M−H]$^-$.

Example 20: Preparation of Boc-Pro-Ala-Ser-OBzl

By following the method of Example 1, 2.92 g (63%) of the title compound as colorless powder was prepared from 3.15 g (11 mmol) Boc-Pro-Ala and 3.67 g (10 mmol) Tos.Ser-OBzl. ESI-MS (m/e): 464 [M+H]$^+$.

Example 21: Preparation of Boc-Pro-Ala-Ser

By following the method of Example 3, 3.28 g (88%) of the title compound was prepared from 4.63 g (10 mmol) Boc-Pro-Ala-Ser-OBzl. ESI-MS (m/e): 372 [M−H]$^-$.

Example 22: Preparation of Boc-Pro-Ala-Ile-OBzl

By following the method of Example 1, 3.33 g (65%) of the title compound as colorless powder was prepared from 3.15 g (11 mmol) Boc-Pro-Ala and 3.93 g (10 mmol) Tos.Ile-OBzl. ESI-MS (m/e): 490 [M+H]$^+$.

Example 23: Preparation of Boc-Pro-Ala-Ile

By following the method of Example 3, 3.67 g (91%) of the title compound was prepared from 4.89 g (10 mmol) Boc-Pro-Ala-Ile-OBzl. ESI-MS (m/e): 398 [M−H]$^-$.

Example 24: Preparation of Boc-Pro-Ala-Thr-OBzl

By following the method of Example 1, 3.39 g (71%) of the title compound as colorless powder was prepared from 3.15 g (11 mmol) Boc-Pro-Ala and 3.81 g (10 mmol) Tos.Thr-OBzl. ESI-MS (m/e): 478 [M+H]$^+$.

Example 25: Preparation of Boc-Pro-Ala-Thr

By following the method of Example 3, 3.56 g (91%) of the title compound was prepared from 4.77 g (10 mmol) Boc-Pro-Ala-Thr-OBzl. ESI-MS (m/e): 386 [M−H]$^-$.

Example 26: Preparation of Boc-Pro-Ala-Lys(Z)-OBzl

By following the method of Example 1, 4.15 g (65%) of the title compound as colorless powder was prepared from 3.15 g (11 mmol) Boc-Pro-Ala and 4.06 g (10 mmol) HCl.Lys(Z)-OBzl. ESI-MS (m/e): 639 [M+H]$^+$.

Example 27: Preparation of Boc-Pro-Ala-Lys(Z)

By following the method of Example 3, 4.71 g (86%) of the title compound was prepared from 6.39 g (10 mmol) Boc-Pro-Ala-Lys(Z)-OBzl. ESI-MS (m/e): 547[M−H]$^-$.

Example 28: Preparation of Boc-Pro-Ala-Leu-OBzl

By following the method of Example 1, 3.37 g (69%) of the title compound as colorless powder was prepared from 3.15 g (11 mmol) Boc-Pro-Ala and 3.93 g (10 mmol) Tos.Leu-OBzl. ESI-MS (m/e): 490 [M+H]$^+$.

Example 29: Preparation of Boc-Pro-Ala-Leu

By following the method of Example 3, 3.67 g (91%) of the title compound was prepared from 4.89 g (10 mmol) Boc-Pro-Ala-Leu-OBzl. ESI-MS (m/e): 398 [M−H]$^-$.

Example 30: Preparation of Boc-Pro-Ala-Gln-OBzl

By following the method of Example 1, 3.23 g (63%) the title compound as colorless powder was prepared from 3.15 g (11 mmol) Boc-Pro-Ala and 2.73 g (10 mmol) HCl.Gln-OBzl. ESI-MS (m/e): 505 [M+H]$^+$.

Example 31: Preparation of Boc-Pro-Ala-Gln

By following the method of Example 3, 3.73 g (90%) of the title compound was prepared from 5.04 g (10 mmol) Boc-Pro-Ala-Gln-OBzl. ESI-MS (m/e): 413 [M−H]$^-$.

Example 32: Preparation of Boc-Pro-Ala-Asn-OBzl

By following the method of Example 1, 3.04 g (61%) of the title compound as colorless powder was prepared from 3.15 g (11 mmol) Boc-Pro-Ala and 2.59 g (10 mmol) HCl.Asn-OBzl. ESI-MS (m/e): 491 [M+H]$^+$.

Example 33: Preparation of Boc-Pro-Ala-Asn

By following the method of Example 3, 3.67 g (92%) of the title compound was prepared from 4.90 g (10 mmol) Boc-Pro-Ala-Asn-OBzl. ESI-MS (m/e): 399 [M−H]$^-$.

Example 34: Preparation of 3S-6,7-dihydroxy-1,1-dimethyl-1,2,3,4-tetrahydro-isoquinoline-3-acyl-carboxylic acid (1)

5.0 g (25 mmol) 3,4-dihydroxy-L-phenylalanine was dissolved in 250 mL acetone, and then 6.0 g (30 mmol) anhydrous magnesium sulfate was added into the obtained solution. After 30 minutes, 25 mL TFA was added thereto on an ice bath. The mixture was stirred at room temperature for 96 hours until the starting material spot was disappeared as shown by TLC (CH$_2$Cl$_2$: MeOH 1:1). The reaction solution was filtered. The filtrate was concentrated under reduced pressure and the residue was dissolved in acetone and continued to be concentrated under reduced pressure for 3 times. 200 mL anhydrous ether was added to the residue to precipitate massive amount of colorless solid. After suction filtration, 5.8 g (95%) of the title compound was obtained as colorless solid. ESI-MS (m/e): 238 [M+H]$^+$; $^1$HNMR (300 MHz, DMSO-d$_6$) δ/ppm=6.61 (s, 1H), 6.45 (s, 1H), 3.70 (dd, J=3.9, 11.4 Hz, 1H), 2.76 (dd, J=11.7, 15.3 Hz, 1H), 2.62 (m, 1H), 1.41 (s, 3H), 1.32 (s, 3H).

Example 35: Preparation of 3S-6,7-dihydroxy-1,1-dimethyl-1,2,3,4-tetrahydro-isoquinoline-3-acyl-Lys (Boc)-OBzl (2)

By following the method of Example 1, 1.19 g (5.01 mmol) 3S-6,7-dihydroxy-1, 1-dimethyl-1,2,3,4-tetrahydro-isoquinoline-3-acyl-carboxylic acid was dissolved in 10 mL of anhydrous DMF. 675 mg (5.00 mmol) N-hydroxybenzotriazole triazole (HOBt) was added to the obtained solution. After 10 minutes, a solution of 1.20 g (5.83 mmol) dicyclohexyl carbodiimide (DCC) and 5 mL anhydrous DMF was added thereto on an ice bath to obtain reaction solution (I). 2.83 g (5.53 mmol) HCl.Lys(Boc)-OBzl was dissolved in 15 mL anhydrous DMF and then stirred for 30 minutes to obtain reaction solution (II). The reaction solution (II) was added into the reaction solution (I) while stirred on an ice bath. The reaction mix was stirred at room temperature for 12 hours, and adjusted to pH=9 using MMM when necessary until 3S-6,7-dihydroxy-1,1-dimethyl-1,2,3,4-tetrahydro-isoquinoline-3-acyl-carboxylic acid disappeared as shown by TLC (CH$_2$Cl$_2$: MeOH 10:1). The reaction mixture was filtered to remove Dicyclohexylurea (DCU). The filtrate was concentrated under reduced pressure to remove DMF. The residue was dissolved in 150 mL EA. The obtained solution was sequentially washed by saturated NaHCO$_3$ aqueous solution for 3 times, and then by saturated NaCl aqueous solution for 3 times. The EA solution was dried by anhydrous Na$_2$SO$_4$, and filtered. The filtrate was concentrated to dry under reduced pressure. The residue was purified by column chromatography (CH$_2$Cl$_2$: MeOH, 50:1) to obtain 327 mg (59%) of the title compound as a light pink powder. ESI-MS (m/e): 556 [M+H]$^+$; $^1$HNMR (300 MHz, DMSO-d$_6$) δ/ppm=8.64 (s, 1H), 8.52 (s, 1H), 8.14 (d, J=7.5 Hz, 1H), 7.36 (m, 5H), 6.74 (m, 1H), 6.57 (s, 1H), 6.37 (s, 1H), 5.14 (m, 2H), 4.30 (m, 1H), 3.55 (m, 2H), 3.32 (m, 2H), 2.88 (m, 2H), 2.57 (d, J=3.9 Hz, 1H), 2.27 (m, 1H), 2.15 (s, 1H), 1.69 (m, 4H), 1.36 (s, 9H), 1.33 (s, 3H), 1.25 (s, 3H).

Example 36: Preparation of 3S-6,7-dihydroxy-1,1-dimethyl-1,2,3,4-tetrahydro-isoquinoline-3-acyl-Lys-OBzl (3A)

By following method of Example 2, 1.01 g (82%) of the title compound as light pink solid was prepared from 1.50 g (2.73 mmol) 3S-6,7-dihydroxy-1, 1-dimethyl-1,2,3,4-tetrahydro-isoquinoline-3-acyl-Lys(Boc)-Obzl, which was directly used in the next reaction. ESI-MS(m/e): 456[M+H]$^+$.

Example 37: Preparation of 3S-6,7-dihydroxy-1,1-dimethyl-1,2,3,4-tetrahydro-isoquinoline-3-acyl-Lys (Boc-Pro-Ala-Ala)-OBzl (4Aa)

By following the method of Example 1, 302 mg (38%) of the title compound as light yellow powder was prepared from 482 mg (1.01 mmol) 3S-6,7-dihydroxy-1,1-dimethyl-1,2,3,4-tetrahydro-isoquinoline-3-acyl-Lys-OBzl and 424 mg (1.20 mmol) Boc-Pro-Ala-Ala. ESI-MS (m/e): 795 [M+H]$^+$; $^1$HNMR (300 MHz, DMSO-d$_6$) δ/ppm=9.15 (s, 1H), 8.89 (s, 2H), 8.11 (m, 1H), 7.94 (m, 1H), 7.85 (m, 1H), 7.76 (m, 1H), 7.44-7.31 (m, 5H), 6.66 (s, 1H), 6.47 (s, 1H), 5.14 (m, 2H), 4.25 (m, 1H), 4.23 (m, 3H), 4.12 (m, 1H), 3.66 (m, 1H), 3.12 (m, 2H), 2.96 (m, 2H), 2.89-2.91 (m, 2H), 2.11-2.08 (m, 1H), 1.77 (m, 5H), 1.59 (s, 3H), 1.47-1.27 (m, 17H), 1.27-1.08 (m, 7H).

Example 38: Preparation of 3S-6,7-dihydroxy-1,1-dimethyl-1,2,3,4-tetrahydro-isoquinoline-3-acyl-Lys (Boc-Pro-Ala-Val)-OBzl (4Ab)

By following the method of Example 1, 604 mg (37%) of the title compound as light yellow powder was prepared from 964 mg (2.01 mmol) 3S-6,7-dihydroxy-1,1-dimethyl-1,2,3,4-tetrahydro-isoquinoline-3-acyl-Lys-OBzl and 924 mg (2.40 mmol) Boc-Pro-Ala-Val. ESI-MS (m/e): 823 [M+H]$^+$; $^1$HNMR (300 MHz, DMSO-d$_6$) δ/ppm=9.18 (s, 1H), 8.93 (m, 2H), 8.05 (m, 2H), 7.42 (m, 5H), 6.66 (s, 1H), 6.47 (s, 1H), 5.16 (s, 1H), 4.37-4.28 (m, 3H), 4.11 (m, 3H), 3.06-2.89 (m, 5H), 2.75 (m, 6H), 2.04 (s, 1H), 1.91 (m, 1H), 1.79 (m, 5H), 1.62 (s, 3H), 1.49 (s, 3H), 1.39 (m, 7H), 1.32 (m, 3H), 1.21 (m, 4H), 0.82 (m, 6H).

Example 39: Preparation of 3S-6,7-dihydroxy-1,1-dimethyl-1,2,3,4-tetrahydro-isoquinoline-3-acyl-Lys (Boc-Pro-Ala-Trp)-OBzl (4Ac)

By following the method of Example 1, 318 mg (35%) of the title compound as light yellow powder was prepared from 482 mg (1.01 mmol) 3S-6,7-dihydroxy-1,1-dimethyl-1,2,3,4-tetrahydro-isoquinoline-3-acyl-Lys-OBzl and 567 mg (1.20 mmol) Boc-Pro-Ala-Trp. ESI-MS (m/e): 910 [M+H]$^+$; $^1$HNMR (300 MHz, DMSO-d$_6$) δ/ppm=9.51 (s, 1H), 9.26 (m, 2H), 8.98 (m, 2H), 8.05 (d, 1H, J=7.2 Hz), 7.94 (m, 1H), 7.78 (d, 1H, J=7.2 Hz), 7.54 (m, 1H), 7.38 (m, 5H), 7.31 (d, 1H, J=4.5 Hz), 7.24 (m, 1H), 7.11 (t, 1H, J=4.5 Hz), 7.05 (t, 1H, J=4.5 Hz), 6.67 (s, 1H), 6.52 (s, 1H), 5.15 (s, 2H), 4.44 (m, 1H), 4.35 (m, 2H), 4.07 (m, 2H), 3.23 (m, 1H), 3.17 (m, 5H), 2.86 (m, 1H), 1.97 (m, 2H), 1.76-1.70 (m, 8H), 1.31 (s, 3H), 1.24 (s, 3H), 1.93-1.79 (m, 9H), 1.16 (m, 4H).

Example 40: Preparation of 3S-6,7-dihydroxy-1,1-dimethyl-1,2,3,4-tetrahydro-isoquinoline-3-acyl-Lys (Boc-Pro-Ala-Tyr)-OBzl (4Ad)

By following the method of Example 1, 549 mg (31%) of the title compound as light yellow powder was prepared from 964 mg (2.01 mmol) 3S-6,7-dihydroxy-1,1-dimethyl-1,2,3,4-tetrahydro-isoquinoline-3-acyl-Lys-OBzl and 1077 mg (2.40 mmol) Boc-Pro-Ala-Tyr. ESI-MS (m/e): 887 [M+H]$^+$; $^1$HNMR (300 MHz, DMSO-d$_6$) δ/ppm=9.17 (m, 1H), 9.02 (m, 1H), 8.73 (m, 1H), 8.51 (m, 1H), 8.09 (m, 1H), 7.97 (m, 1H), 7.73 (m, 1H), 7.40 (m, 5H), 6.96 (m, 2H), 6.61 (m, 3H), 6.48 (s, 1H), 5.16 (s, 2H), 4.23 (m, 2H), 4.07 (m, 2H), 3.88 (m, 1H), 3.01 (m, 3H), 2.74 (m, 3H), 2.02 (m, 2H), 1.74 (m, 5H), 1.46 (s, 3H), 1.36-1.24 (m, 16H), 1.16 (m, 3H), 0.87 (m, 1H).

Example 41: Preparation of 3S-6,7-dihydroxy-1,1-dimethyl-1,2,3,4-tetrahydro-isoquinoline-3-acyl-Lys (Boc-Pro-Ala-Pro)-OBzl (4Ae)

By following the method of Example 1, 607 mg (37%) of the title compound as light yellow powder was prepared from 964 mg (2.01 mmol) 3S-6,7-dihydroxy-1,1-dimethyl-1,2,3,4-tetrahydro-isoquinoline-3-acyl-Lys-OBzl and 957 mg (2.40 mmol) Boc-Pro-Ala-Pro. ESI-MS (m/e): 821 [M+H]$^+$; $^1$HNMR (300 MHz, DMSO-d$_6$) δ/ppm=9.54 (m, 1H), 9.23 (s, 1H), 9.11 (m, 1H), 8.96 (s, 1H), 8.05 (m, 1H), 7.85 (m, 1H), 7.40 (m, 5H), 6.67 (s, 1H), 6.48 (s, 1H), 5.16 (m, 2H), 4.54 (m, 1H), 4.38 (m, 2H), 4.24 (m, 1H), 4.10 (m, 2H), 3.55 (m, 1H), 3.17 (m, 3H), 3.05 (m, 3H), 2.94 (m, 1H), 1.96 (m, 2H), 1.79 (m, 7H), 1.64 (s, 3H), 1.51 (s, 3H), 1.38-1.32 (m, 13H), 1.20 (m, 4H).

Example 42: Preparation of 3S-6,7-dihydroxy-1,1-dimethyl-1,2,3,4-tetrahydro-isoquinoline-3-acyl-Lys (Boc-Pro-Ala-Phe)-OBzl (4Af)

By following the method of Example 1, 626 mg (36%) of the title compound as light yellow powder was prepared from 964 mg (2.01 mmol) 3S-6,7-dihydroxy-1,1-dimethyl-1,2,3,4-tetrahydro-isoquinoline-3-acyl-Lys-OBzl and 1039 mg (2.40 mmol) Boc-Pro-Ala-Phe. ESI-MS (m/e): 871 [M+H]$^+$; $^1$HNMR (300 MHz, DMSO-d$_6$) δ/ppm=9.24 (s, 1H), 9.09 (m, 2H), 8.96 (s, 1H), 8.01-7.93 (m, 3H), 7.38 (m, 5H), 7.21 (m, 5H), 6.67 (s, 1H), 6.49 (s, 1H), 5.17 (s, 2H), 4.38 (m, 3H), 4.09 (m, 2H), 3.28 (m, 4H), 2.88 (m, 2H), 2.79 (m, 5H), 1.99 (m, 2H), 1.74 (m, 8H), 1.50 (m, 3H), 1.32 (m, 14H), 1.16 (m, 4H).

Example 43: Preparation of 3S-6,7-dihydroxy-1,1-dimethyl-1,2,3,4-tetrahydro-isoquinoline-3-acyl-Lys (Boc-Pro-Ala-Gly)-OBzl (4Ag)

By following the method of Example 1, 304 mg (39%) of the title compound as light yellow powder was prepared from 482 mg (1.01 mmol) 3S-6,7-dihydroxy-1,1-dimethyl-1,2,3,4-tetrahydro-isoquinoline-3-acyl-Lys-OBzl and 412 mg (1.20 mmol) Boc-Pro-Ala-Gly. ESI-MS (m/e): 781 [M+H]$^+$; $^1$HNMR (300 MHz, DMSO-d$_6$) δ/ppm=9.39 (s, 1H), 8.97 (m, 2H), 8.24-8.14 (m, 2H), 7.79 (m, 1H), 7.41 (m, 5H), 6.66 (s, 1H), 6.47 (s, 1H), 5.16 (s, 2H), 4.35 (m, 2H), 4.21 (m, 2H), 3.71-3.66 (m, 2H), 3.03 (m, 3H), 2.89-2.76 (m, 1H), 2.07 (m, 1H), 1.81-1.77 (m, 6H), 1.62 (s, 3H), 1.50 (s, 3H), 1.38 (m, 7H), 1.32 (m, 8H), 1.23 (m, 4H).

Example 44: Preparation of 3S-6,7-dihydroxy-1,1-dimethyl-1,2,3,4-tetrahydro-isoquinoline-3-acyl-Lys (Boc-Pro-Ala-Ser)-OBzl (4Ah)

By following the method of Example 1, 454 mg (29%) of the title compound as light yellow powder was prepared from 965 mg (2.01 mmol) 3S-6,7-dihydroxy-1,1-dimethyl-1,2,3,4-tetrahydro-isoquinoline-3-acyl-Lys-OBzl and 896 mg (2.40 mmol) Boc-Pro-Ala-Ser. ESI-MS (m/e): 811 [M+H]$^+$; $^1$HNMR (300 MHz, DMSO-d$_6$) δ/ppm=9.48 (m, 1H), 9.23 (s, 2H), 8.96 (m, 1H), 8.19 (m, 1H), 7.40 (m, 5H), 6.67 (s, 1H), 6.48 (s, 1H), 5.16 (m, 2H), 4.92 (m, 1H), 4.31 (m, 3H), 4.13 (m, 3H), 3.53 (m, 2H), 3.16 (m, 3H), 3.04-2.81 (m, 4H), 2.08 (m, 1H), 1.78 (m, 5H), 1.63 (s, 3H), 1.51 (s, 3H), 1.39-1.32 (m, 14H), 1.22 (m, 3H).

Example 45: Preparation of 3S-6,7-dihydroxy-1,1-dimethyl-1,2,3,4-tetrahydro-isoquinoline-3-acyl-Lys (Boc-Pro-Ala-Ile)-OBzl (4Ai)

By following the method of Example 1, 310 mg (37%) of the title compound as light yellow powder was prepared from 482 mg (1.01 mmol) 3S-6,7-dihydroxy-1,1-dimethyl-1,2,3,4-tetrahydro-isoquinoline-3-acyl-Lys-OBzl and 479 mg (1.20 mmol) Boc-Pro-Ala-Ile. ESI-MS (m/e): 837 [M+H]$^+$; $^1$HNMR (300 MHz, DMSO-d$_6$) δ/ppm=8.84-8.68 (m, 2H), 8.37 (s, 1H), 7.99-7.87 (m, 3H), 7.39 (m, 4H), 6.60 (s, 1H), 6.39 (s, 1H), 5.14 (m, 2H), 4.32 (m, 2H), 4.17 (m, 2H), 3.65 (m, 1H), 3.54 (m, 1H), 3.17 (m, 1H), 2.96 (m, 2H), 2.68 (m, 3H), 2.11 (m, 1H), 1.74-1.68 (m, 7H), 1.31-1.21 (m, 11H), 1.17 (m, 5H), 1.08 (m, 1H), 0.82 (m, 8H).

Example 46: Preparation of 3S-6,7-dihydroxy-1,1-dimethyl-1,2,3,4-tetrahydro-isoquinoline-3-acyl-Lys (Boc-Pro-Ala-Thr)-OBzl (4Aj)

By following the method of Example 1, 495 mg (30%) of the title compound as light yellow powder was prepared from 964 mg (2.01 mmol) 3S-6,7-dihydroxy-1,1-dimethyl-1,2,3,4-tetrahydro-isoquinoline-3-acyl-Lys-OBzl and 929 mg (2.40 mmol) Boc-Pro-Ala-Thr. ESI-MS (m/e): 825 [M+H]$^+$; $^1$HNMR (300 MHz, DMSO-d$_6$) δ/ppm=9.18 (s, 1H), 8.91 (s, 2H), 8.27 (m, 1H), 7.64 (m, 1H), 7.41 (m, 6H), 6.65 (s, 1H), 6.48 (s, 1H), 5.16 (s, 2H), 4.35 (m, 3H), 4.23 (m, 3H), 3.07 (m, 3H), 2.72 (m, 1H), 1.83-1.76 (m, 5H), 1.61 (s, 3H), 1.48 (s, 3H), 1.38-1.32 (m, 14H), 1.23 (m, 3H), 1.11 (m, 3H).

Example 47: Preparation of 3S-6,7-dihydroxy-1,1-dimethyl-1,2,3,4-tetrahydro-isoquinoline-3-acyl-Lys [Boc-Pro-Ala-Lys(Z)]-OBzl (4Ak)

By following the method of Example 1, 750 mg (30%) of the title compound as light yellow powder was prepared from 964 mg (2.01 mmol) 3S-6,7-dihydroxy-1,1-dimethyl-1,2,3,4-tetrahydro-isoquinoline-3-acyl-Lys-OBzl and 1209 mg (2.40 mmol) Boc-Pro-Ala-Lys(Z). ESI-MS (m/e): 987 [M+H]$^+$; $^1$HNMR (300 MHz, DMSO-d$_6$) δ/ppm=8.68 (s, 1H), 8.56 (s, 1H), 8.16 (m, 1H), 8.04 (m, 1H), 7.78 (m, 1H), 7.68 (m, 1H), 7.34 (m, 10H), 6.58 (s, 1H), 6.37 (s, 1H), 5.14 (s, 2H), 4.98 (s, 2H), 4.29 (m, 2H), 4.09 (m, 3H), 3.56 (m, 3H), 3.01 (m, 4H), 2.62 (m, 1H), 2.40 (m, 1H), 2.27 (m, 1H), 2.15 (s, 1H), 2.06 (m, 1H), 2.01 (s, 1H), 1.78 (m, 6H), 1.38-1.31 (m, 18H), 1.17 (m, 10H).

Example 48: Preparation of 3S-6,7-dihydroxy-1,1-dimethyl-1,2,3,4-tetrahydro-isoquinoline-3-acyl-Lys (Boc-Pro-Ala-Leu)-OBzl (4Al)

By following the method of Example 1, 301 mg (36%) of the title compound as light yellow powder was prepared from 482 mg (1.01 mmol) 3S-6,7-dihydroxy-1,1-dimethyl-1,2,3,4-tetrahydro-isoquinoline-3-acyl-Lys-OBzl and 479 mg (1.20 mmol) Boc-Pro-Ala-Leu. ESI-MS (m/e): 837 [M+H]$^+$; $^1$HNMR (300 MHz, DMSO-d$_6$) δ/ppm=8.69-8.57 (m, 2H), 8.18-8.06 (m, 2H), 7.85 (m, 1H), 7.69 (m, 5H), 6.58 (s, 1H), 6.37 (s, 1H), 5.14 (m, 2H), 4.25-4.11 (m, 5H), 3.63-3.55 (m, 1H), 3.17 (s, 2H), 3.04-2.98 (m, 2H), 2.64-2.59 (m, 1H), 2.15-2.07 (m, 1H), 1.78-1.67 (m, 5H), 1.36 (m, 14H), 1.28 (m, 4H), 1.19 (m, 6H).

Example 49: Preparation of 3S-6,7-dihydroxy-1,1-dimethyl-1,2,3,4-tetrahydro-isoquinoline-3-acyl-Lys (Boc-Pro-Ala-Gln)-OBzl (4Am)

By following the method of Example 1, 665 mg (39%) of the title compound as light yellow powder was prepared from 965 mg (2.01 mmol) 3S-6,7-dihydroxy-1,1-dimethyl-1,2,3,4-tetrahydro-isoquinoline-3-acyl-Lys-OBzl and 994 mg (2.40 mmol) Boc-Pro-Ala-Gln. ESI-MS (m/e): 852 [M+H]$^+$; $^1$HNMR (300 MHz, DMSO-d$_6$) δ/ppm=9.3-9.1

(m, 4H), 8.16 (m, 1H), 7.96 (m, 2H), 7.83 (m, 1H), 7.44-7.38 (m, 7H), 6.89 (s, 1H), 6.86 (s, 1H), 6.56 (s, 1H), 5.17 (s, 2H), 4.4-4.1 (m, 6H), 3.17 (m, 4H), 2.98-2.83 (m, 2H), 2.08 (m, 4H), 1.91 (m, 1H), 1.64 (s, 3H), 1.51 (s, 3H), 1.38-1.31 (m, 17H), 1.22-1.20 (m, 4H).

Example 50: Preparation of 3S-6,7-dihydroxy-1,1-dimethyl-1,2,3,4-tetrahydro-isoquinoline-3-acyl-Lys (Boc-Pro-Ala-Asn)-OBzl (4An)

By following the method of Example 1, 636 mg (38%) of the title compound as light yellow powder was prepared from 965 mg (2.01 mmol) 3S-6,7-dihydroxy-1,1-dimethyl-1,2,3,4-tetrahydro-isoquinoline-3-acyl-Lys-OBzl and 960 mg (2.40 mmol) Boc-Pro-Ala-Asn. ESI-MS (m/e): 838 [M+H]$^+$; $^1$HNMR (300 MHz, DMSO-d$_6$) δ/ppm=9.26 (s, 1H), 9.04 (m, 2H), 8.31 (m, 1H), 8.03 (m, 1H), 7.57 (m, 1H), 7.44 (m, 6H), 6.90 (m, 1H), 6.68 (s, 1H), 6.49 (s, 1H), 5.16 (s, 2H), 4.45-4.40 (m, 3H), 4.14 (m, 2H), 3.42 (m, 5H), 3.17 (m, 3H), 2.89-2.82 (m, 1H), 2.09 (m, 1H), 1.90 (m, 1H), 1.79-1.74 (m, 6H), 1.64 (s, 3H), 1.52 (s, 3H), 1.39-1.32 (m, 15H), 1.22 (m, 3H).

Example 51: Preparation of 3S-6,7-dihydroxy-1,1-dimethyl-1,2,3,4-tetrahydro-isoquinoline-3-acyl-Lys [Boc-Pro-Ala-Asp(OBzl)]-OBzl (4Ao)

By following the method of Example 1, 403 mg (35%) of the title compound as light yellow powder was prepared from 870 mg (1.24 mmol) 3S-6,7-dihydroxy-1, 1-dimethyl-1,2,3,4-tetrahydro-isoquinoline-3-acyl-Lys[Asp(OBzl)]-OBzl and 429 mg (2.48 mmol) Boc-Pro-Ala. ESI-MS (m/e): 929 [M+H]$^+$; $^1$HNMR (300 MHz, DMSO-d$_6$) δ/ppm=8.32 (m, 1H), 8.10 (m, 1H), 7.96 (m, 1H), 7.36 (m, 10H), 6.60 (s, 1H), 6.39 (s, 1H), 5.14 (s, 2H), 5.06 (s, 2H), 4.57 (m, 1H), 4.32 (m, 1H), 4.23 (m, 1H), 4.11 (m, 2H), 3.74 (m, 1H), 3.55 (m, 1H), 3.34-3.28 (m, 2H), 3.00 (m, 2H), 2.89 (s, 1H), 2.81 (m, 1H), 2.73 (m, 2H), 2.58 (m, 1H), 2.16-2.06 (m, 1H), 1.91 (s, 2H), 1.75 (m, 5H), 1.40-1.32 (m, 22H), 1.17 (m, 3H).

Example 52: Preparation of 3S-6,7-dihydroxy-1,1-dimethyl-1,2,3,4-tetrahydro-isoquinoline-3-acyl-Lys [Boc-Pro-Ala-Glu(OBzl)]-OBzl (4Ap)

By following the method of Example 1, 269 mg (38%) of the title compound as light yellow powder was prepared from 530 mg (0.75 mmol) 3S-6,7-dihydroxy-1,1-dimethyl-1,2,3,4-tetrahydro-isoquinoline-3-acyl-Lys[Glu (OBzl)]-OBzl and 256 mg (0.90 mmol) Boc-Pro-Ala. ESI-MS (m/e): 943 [M+H]$^+$; $^1$HNMR (300 MHz, DMSO-d$_6$) δ/ppm=9.26 (s, 1H), 9.10 (m, 1H), 8.97 (s, 1H), 8.79-7.88 (m, 3H), 7.36 (m, 10H), 6.67 (s, 1H), 6.48 (s, 1H), 5.14 (s, 2H), 5.06 (s, 2H), 4.35 (m, 1H), 4.23 (m, 2H), 4.10 (m, 1H), 3.83 (s, 1H), 3.34 (m, 5H), 2.83 (m, 1H), 2.72 (m, 1H), 2.34 (m, 2H), 1.78 (m, 10H), 1.51 (s, 3H), 1.36-1.31 (m, 14H), 1.21 (m, 3H).

Example 53: Preparation of 3S-6,7-dihydroxy-1,1-dimethyl-1,2,3,4-tetrahydro-isoquinoline-3-acyl-Lys (Pro-Ala-Ala) (5Aa)

First, the benzyl ester group was removed from 300 mg (0.38 mmol) of 3S-6,7-dihydroxy-1,1-dimethyl-1,2,3,4-tetrahydro-isoquinoline-3-acyl-Lys(Boc-Pro-Ala-Ala)-OBzl by following the method of Example 4. Next, Boc was removed by following the method of Example 2 to give 266 mg (78%) of the title compound as colorless powder. p 207.2-209.4° C.; [α]$_D^{25}$=−4.5 (c=0.25, CH$_3$OH); ESI-MS (m/e): 630 [M−H]$^-$; IR(KBr): 3221.1, 3057.2, 2983.8, 2943.3, 2362.8, 1660.7, 1546.9, 1533.4, 1448.5, 1379.1, 1240.2, 1049.3, 867.9, 659.7; $^1$HNMR (300 MHz, D$_2$O) δ/ppm=6.79 (s, 1H), 6.68 (s, 1H), 4.36-4.29 (m, 5H), 3.32-3.12 (m, 6H), 1.89 (m, 4H), 1.70 (s, 3H), 1.57 (s, 3H), 1.48 (m, 2H), 1.33 (m, 9H).

Example 54: Preparation of 3S-6,7-dihydroxy-1,1-dimethyl-1,2,3,4-tetrahydro-isoquinoline-3-acyl-Lys (Pro-Ala-Val) (5Ab)

By following the method of Example 53, 187 mg (81%) of the title compound as colorless powder was prepared from 300 mg (0.36 mmol) 3S-6,7-dihydroxy-1,1-dimethyl-1,2,3,4-tetrahydro-isoquinoline-3-acyl-Lys(Boc-Pro-Ala-Val)-OBzl. Mp 195.8-197.9° C.; [α]$_D^{25}$=−3.5 (c=0.25, CH$_3$OH); ESI-MS (m/e): 630 [M−H]$^-$; IR(KBr): 3221.1, 3062.9, 2970.4, 1658.8, 1546.9, 1533.4, 1450.5, 1384.9, 1240.2, 1047.4, 991.41, 866.04, 671.2; $^1$HNMR (300 MHz, D$_2$O) δ/ppm=8.13 (m, 1H), 6.79 (s, 1H), 6.68 (s, 1H), 4.36-4.29 (m, 4H), 3.89 (m, 1H), 3.36 (m, 2H), 3.23 (m, 2H), 3.08 (m, 2H), 1.89 (m, 4H), 1.70 (s, 3H), 1.57 (s, 3H), 1.48 (m, 1H), 1.37 (m, 6H), 1.32 (m, 2H), 0.89 (m, 6H).

Example 55: Preparation of 3S-6,7-dihydroxy-1,1-dimethyl-1,2,3,4-tetrahydro-isoquinoline-3-acyl-Lys (Pro-Ala-Trp) (5Ac)

By following the method of Example 53, 180 mg (76%) of the title compound as light pink powder was prepared from 300 mg (0.33 mmol) 3S-6,7-dihydroxy-1,1-dimethyl-1,2,3,4-tetrahydro-isoquinoline-3-acyl-Lys(Boc-Pro-Ala-Trp)-OBzl. Mp 205.1-207.9° C.; [α]$_D^{25}$=−1.3 (c=0.25, CH$_3$OH); ESI-MS (m/e): 718 [M−H]$^-$; IR(KBr): 3221.2, 3059.1, 2981.9, 2941.4, 1660.7, 1533.4, 1448.5, 1388.7, 1240.2, 867.9, 748.4, 630.7; $^1$HNMR (300 MHz, D$_2$O) δ/ppm=7.50 (d, J=7.8 Hz, 1H), 7.39 (d, J=7.8 Hz, 1H), 7.12 (t, J=7.2 Hz, 1H), 7.05 (t, J=7.2 Hz, 1H), 6.74 (s, 1H), 6.62 (s, 1H), 4.38 (m, 1H), 4.35 (m, 1H), 4.27 (m, 1H), 4.18 (m, 2H), 3.24 (m, 2H), 3.16 (m, 3H), 3.06 (m, 3H), 1.83 (m, 1H), 1.68 (m, 4H), 1.47 (m, 3H), 1.37 (m, 2H), 1.25 (m, 3H), 1.21 (m, 3H).

Example 56: Preparation of 3S-6,7-dihydroxy-1,1-dimethyl-1,2,3,4-tetrahydro-isoquinoline-3-acyl-Lys (Pro-Ala-Tyr) (5Ad)

By following the method of Example 53, 174 mg (74%) of the title compound as light yellow powder was prepared from 303 mg (0.34 mmol) 3S-6,7-dihydroxy-1,1-dimethyl-1,2,3,4-tetrahydro-isoquinoline-3-acyl-Lys(Boc-Pro-Ala-Tyr)-OBzl. Mp 200.5-202.8° C.; [α]$_D^{25}$=−2.3 (c=0.25, CH$_3$OH); ESI-MS (m/e): 695 [M−H]$^-$; IR(KBr): 3215.3, 3055.2, 2983.8, 2947.2, 1658.8, 1548.8, 1523.8, 1448.5, 1384.9, 1238.3, 1163.1, 657.7; $^1$HNMR (300 MHz, D$_2$O) δ/ppm=6.98 (m, 2H), 6.92 (m, 3H), 6.65 (s, 1H), 4.34-4.26 (m, 6H), 3.27 (m, 2H), 3.15 (m, 1H), 3.08 (m, 1H), 2.96 (m, 2H), 2.85 (m, 12H), 1.89 (m, 5H), 1.70 (s, 3H), 1.51 (m, 3H), 1.33 (m, 3H), 1.25 (m, 4H).

Example 57: Preparation of 3S-6,7-dihydroxy-1,1-dimethyl-1,2,3,4-tetrahydro-isoquinoline-3-acyl-Lys (Pro-Ala-Pro) (5Ae)

By following the method of Example 53, 179 mg (78%) of the title compound as light yellow powder was prepared from 301 mg (0.36 mmol) 3S-6,7-dihydroxy-1,1-dimethyl- 1,2,3,4-tetrahydro-isoquinoline-3-acyl-Lys(Boc-Pro-Ala-Pro)-OBzl. Mp 204.8-205.4° C.; $[\alpha]_D^{25}$=−5.0 (c=0.25, CH$_3$OH); ESI-MS (m/e): 629 [M−H]$^-$; IR(KBr): 3244.3, 3070.7, 2980.1, 2947.2, 1662.6, 1639.5, 1554.6, 1450.5, 1379.1, 1246.1, 1201.6, 1047.3, 995.3, 871.8, 657.7; $^1$HNMR (300 MHz, D$_2$O) δ/ppm=6.78 (s, 1H), 6.68 (s, 1H), 4.57 (m, 1H), 4.39-4.33 (m, 5H), 3.74 (m, 1H), 3.60 (m, 1H), 3.26 (m, 2H), 3.17 (m, 1H), 3.04 (m, 2H), 2.19 (m, 3H), 1.85 (m, 5H), 1.69 (m, 4H), 1.54 (m, 6H), 1.36 (m, 6H).

Example 58: Preparation of 3S-6,7-dihydroxy-1,1-dimethyl-1,2,3,4-tetrahydro-isoquinoline-3-acyl-Lys (Pro-Ala-Phe) (5Af)

By following the method of Example 53, 183 mg (78%) of the title compound as light yellow powder was prepared from 300 mg (0.34 mmol) 3S-6,7-dihydroxy-1,1-dimethyl-1,2,3,4-tetrahydro-isoquinoline-3-acyl-Lys(Boc-Pro-Ala-Phe)-OBzl. Mp 175.8-178.2° C.; $[\alpha]_D^{25}$=−3.3 (c=0.25, CH$_3$OH); ESI-MS (m/e): 679 [M−H]$^-$; IR(KBr): 3215.3, 3049.5, 2949.2, 1662.6, 1539.2, 1454.3, 1394.5; $^1$HNMR (300 MHz, D$_2$O) δ/ppm=7.26 (m, 3H), 7.14 (m, 2H), 6.77 (s, 1H), 6.65 (s, 1H), 4.39-4.33 (m, 3H), 4.03 (m, 3H), 3.42 (m, 1H), 3.37 (m, 1H), 3.29 (m, 2H), 3.17 (m, 1H), 3.09 (m, 4H), 2.95 (m, 3H), 1.91 (m, 5H), 1.74 (s, 3H), 1.53 (s, 3H), 1.33 (m, 6H).

Example 59: Preparation of 3S-6,7-dihydroxy-1,1-dimethyl-1,2,3,4-tetrahydro-isoquinoline-3-acyl-Lys (Pro-Ala-Gly) (5Ag)

By following the method of Example 53, 193 mg (85%) of the title compound as colorless powder was prepared from 300 mg (0.38 mmol) S-6,7-dihydroxy-1,1-dimethyl-1,2,3,4-tetrahydro-isoquinoline-3-acyl-Lys(Boc-Pro-Ala-Gly)-OBzl. Mp 196.4-199.5° C.; $[\alpha]_D^{25}$=−3.0 (c=0.25, CH$_3$OH); ESI-MS (m/e): 588 [M−H]$^-$; IR(KBr): 3223.1, 3062.9, 2983.8, 1630.2, 1552.7, 1537.3, 1448.5, 1382.9, 1244.1, 1049.3, 1006.8, 869.9, 661.6; $^1$HNMR (300 MHz, D$_2$O) δ/ppm=6.77 (s, 1H), 6.67 (s, 1H), 4.34-4.28 (m, 4H), 3.78 (s, 2H), 3.30 (m, 2H), 3.15 (m, 3H), 1.92 (m, 3H), 1.70 (s, 3H), 1.55 (s, 3H), 1.33 (m, 6H).

Example 60: Preparation of 3S-6,7-dihydroxy-1,1-dimethyl-1,2,3,4-tetrahydro-isoquinoline-3-acyl-Lys (Pro-Ala-Ser) (5Ah)

By following the method of Example 53, 181 mg (79%) of the title compound as light yellow powder was prepared from 300 mg (0.37 mmol) 3S-6,7-dihydroxy-1,1-dimethyl-1,2,3,4-tetrahydro-isoquinoline-3-acyl-Lys(Boc-Pro-Ala-Ser)-OBzl. Mp 195.6-197.4° C.; $[\alpha]_D^{25}$=−3.8 (c=0.25, CH$_3$OH); ESI-MS (m/e): 619 [M−H]$^-$; IR(KBr): 3228.8, 3061.0, 2981.9, 2943.4, 1732.1, 1662.6, 1550.7 1533.3, 1448.5, 1384.9, 1244.1, 1159.2, 1049.3, 869.9, 657.7, 518.8; $^1$HNMR (300 MHz, D$_2$O) δ/ppm=6.78 (s, 1H), 6.67 (s, 1H), 4.41-4.26 (m, 5H), 3.74 (m, 2H), 3.25-3.13 (m, 6H), 1.91 (m, 3H), 1.69 (s, 3H), 1.55 (m, 3H), 1.46 (m, 2H), 1.37 (m, 6H).

Example 61: Preparation of 3S-6,7-dihydroxy-1,1-dimethyl-1,2,3,4-tetrahydro-isoquinoline-3-acyl-Lys (Pro-Ala-Ile) (5Ai)

By following the method of Example 53, 181 mg (78%) of the title compound as colorless powder was prepared from 302 mg (0.36 mmol) 3S-6,7-dihydroxy-1, 1-dimethyl-1,2,3,4-tetrahydro-isoquinoline-3-acyl-Lys(Boc-Pro-Ala-Ile)-OBzl. Mp 175.6-178.4° C.; $[\alpha]_D^{25}$=−3.3 (c=0.25, CH$_3$OH); ESI-MS (m/e): 645 [M−H]$^-$; IR(KBr): 3224.9, 3057.2, 2970.4, 2758.2, 2497.8, 2360.87, 1656.9, 1535.3, 1454.3, 1388.7, 1244.1, 1159.1, 1037.7, 871.8, 659.6; $^1$HNMR (300 MHz, D$_2$O) δ/ppm=6.79 (s, 1H), 6.68 (s, 1H), 4.42 (m, 1H), 4.35 (m, 1H), 4.29 (m, 1H), 4.18 (m, 1H), 3.92 (d, J=1.2 Hz, 1H), 3.31 (m, 2H), 3.19 (m, 2H), 3.10 (m, 3H), 2.34 (m, 1H), 2.12 (m, 1H), 1.74 (m, 4H), 1.57 (m, 3H), 1.36 (m, 6H), 1.21 (m, 2H), 0.84 (m, 9H).

Example 62: Preparation of 3S-6,7-dihydroxy-1,1-dimethyl-1,2,3,4-tetrahydro-isoquinoline-3-acyl-Lys (Pro-Ala-Thr) (5Aj)

By following the method of Example 53, 175 mg (76%) of the title compound as light yellow powder was prepared from 300 mg (0.36 mmol) 3S-6,7-dihydroxy-1,1-dimethyl-1,2,3,4-tetrahydro-isoquinoline-3-acyl-Lys(Boc-Pro-Ala-Thr)-OBzl. Mp 194.8-197.5° C.; $[\alpha]_D^{25}$=−2.8 (c=0.25, CH$_3$OH); ESI-MS (m/e): 633 [M−H]$^-$; IR(KBr): 3236.5, 3066.8, 2933.7, 1660.7, 1548.8, 1533.4, 1450.8, 1381.0, 1240.2, 1157.3, 1049.3, 869.9, 669.3; $^1$HNMR (300 MHz, D$_2$O) δ/ppm=6.81 (s, 1H), 6.71 (s, 1H), 4.43-4.31 (m, 4H), 4.11 (m, 2H), 3.33 (m, 2H), 3.24 (m, 1H), 3.24 (m, 2H), 3.21 (m, 1H), 3.18 (m, 1H), 3.09 (m, 1H), 1.94 (m, 3H), 1.74 (s, 3H), 1.58 (s, 3H), 1.51 (m, 2H), 1.23 (m, 1H), 1.19 (m, 1H), 1.14 (m, 3H).

Example 63: Preparation of 3S-6,7-dihydroxy-1,1-dimethyl-1,2,3,4-tetrahydro-isoquinoline-3-acyl-Lys (Pro-Ala-Lys) (5Ak)

By following the method of Example 53, 152 mg (75%) of the title compound as dark yellow powder was prepared from 305 mg (0.31 mmol) 3S-6,7-dihydroxy-1,1-dimethyl-1,2,3,4-tetrahydro-isoquinoline-3-acyl-Lys[Boc-Pro-Ala-Lysl(Z)]-OBzl. Mp 185.6-188.1° C.; $[\alpha]_D^{25}$=−1.8 (c=0.25, CH$_3$OH); ESI-MS (m/e): 660 [M−H]$^-$; IR(KBr): 3853.7, 3738.1, 2956.8, 2349.3, 2017.5, 1668.4, 1537.3, 1400.3, 1257.6, 1043.5, 871.8, 671.2; $^1$HNMR (300 MHz, D$_2$O) δ/ppm=6.80 (s, 1H), 6.69 (s, 1H), 4.45 (m, 1H), 4.35 (m, 1H), 4.29 (m, 1H), 4.18 (m, 2H), 3.73 (m, 2H), 3.22-3.13 (m, 8H), 3.09 (m, 4H), 2.95 (m, 1H), 1.93 (m, 6H), 1.74 (m, 9H), 1.58 (m, 6H), 1.47 (m, 2H), 1.32-1.27 (m, 16H), 1.18 (m, 2H).

Example 64: Preparation of 3S-6,7-dihydroxy-1,1-dimethyl-1,2,3,4-tetrahydro-isoquinoline-3-acyl-Lys (Pro-Ala-Leu) (5Al)

By following the method of Example 53, 178 mg (77%) of the title compound as colorless powder was prepared from 300 mg (0.36 mmol) 3S-6,7-dihydroxy-1,1-dimethyl-1,2,3,4-tetrahydro-isoquinoline-3-acyl-Lys(Boc-Pro-Ala-L IR(KBr): 3224.9, 3064.9, 2956.8, 1660.7, 1548.8, 1535.3, 1448.5, 1381.0, 1242.2, 1049.3, 997.2, 869.9, 669.3; $^1$HNMR (300 MHz, D$_2$O) δ/ppm=6.78 (s, 1H), 6.68 (s, 1H), 4.38-4.29 (m, 3H), 4.13 (m, 2H), 3.31 (m, 3H), 3.21 (m, 1H), 3.08 (m, 2H), 1.89 (m, 4H), 1.70 (s, 3H), 1.57 (m, 4H), 1.46 (m, 5H), 1.32 (m, 6H), 1.32 (m, 1H), 1.16 (m, 6H).

Example 65: Preparation of 3S-6,7-dihydroxy-1,1-dimethyl-1,2,3,4-tetrahydro-isoquinoline-3-acyl-Lys (Pro-Ala-Gln) (5Am)

By following the method of Example 53, 184 mg (79%) of the title compound as colorless powder was prepared from 300 mg (0.35 mmol) 3S-6,7-dihydroxy-1,1-dimethyl-1,2,3,4-tetrahydro-isoquinoline-3-acyl-Lys(Boc-Pro-Ala-Gln)-OBzl. Mp 181.3-183.3° C.; $[\alpha]_D^{25}$=−3.0 (c=0.25, CH$_3$OH); ESI-MS (m/e): 660 [M−H]$^-$; IR(KBr): 3213.4, 3059.1, 2981.9, 2943.4, 2362.8, 1739.8, 1662.6, 1548.8, 1537.3, 1450.5, 1375.3, 1244.1, 1047.2, 871.8, 659.7; $^1$HNMR (300 MHz, D$_2$O) δ/ppm=6.80 (s, 1H), 6.69 (s, 1H), 4.40-4.29 (m, 5H), 3.33 (m, 3H), 3.17 (m, 3H), 1.90 (m, 2H), 1.69 (s, 3H), 1.55 (s, 3H), 1.43 (m, 2H), 1.31 (m, 8H).

Example 66: Preparation of 3S-6,7-dihydroxy-1,1-dimethyl-1,2,3,4-tetrahydro-isoquinoline-3-acyl-Lys (Pro-Ala-Asn) (5An)

By following the method of Example 53, of 174 mg (78%) of the title compound as colorless powder was prepared from 302 mg (0.36 mmol) 3S-6,7-dihydroxy-1,1-dimethyl-1,2,3,4-tetrahydro-isoquinoline-3-acyl-Lys(Boc-Pro-Ala-A sn)-OBzl. Mp 202.5-204.7° C.; $[\alpha]_D^{25}$=−2.3 (c=0.25, CH$_3$OH); ESI-MS (m/e): 646 [M−H]$^-$; IR(KBr): 3207.6, 3059.1, 2943.3, 1674.2, 1537.3, 1448.5, 1381.0, 1247.9, 642.3; $^1$HNMR (300 MHz, D$_2$O) δ/ppm=6.78 (s, 1H), 6.67 (s, 1H), 4.48 (m, 1H), 4.42-4.29 (m, 4H), 3.29 (m, 2H), 3.16 (m, 4H), 2.65 (m, 2H), 1.90 (m, 2H), 1.69 (s, 3H), 1.55 (s, 3H), 1.31 (m, 6H).

Example 67: Preparation of 3S-6,7-dihydroxy-1,1-dimethyl-1,2,3,4-tetrahydro-isoquinoline-3-acyl-Lys (Pro-Ala-Asp) (5Ao)

By following the method of Example 53, of 174 mg (83%) of the title compound as colorless powder was prepared from 300 mg (0.32 mmol) 3S-6,7-dihydroxy-1,1-dimethyl-1,2,3,4-tetrahydro-isoquinoline-3-acyl-Lys-[Boc-Pro-Ala-Asp(OBzl)]-OBzl. Mp 207.1-209.7° C.; $[\alpha]_D^{25}$=−3.5 (c=0.25, CH$_3$OH); ESI-MS (m/e): 647 [M−H]$^-$; IR(KBr): 3383.3, 3061.0, 2360.9, 1670.3, 1550.8, 1448.5, 1400.3, 1246.3, 873.8, 611.4; $^1$HNMR (300 MHz, D$_2$O) δ/ppm=6.76 (s, 1H), 6.66 (s, 1H), 4.52 (m, 1H), 4.37-4.281 (m, 4H), 3.27 (m, 4H), 3.13 (m, 1H), 3.05 (m, 1H), 2.76 (m, 2H), 1.97 (m, 1H), 1.90 (m, 1H), 1.71 (s, 3H), 1.55 (s, 3H), 1.43 (m, 2H), 1.31 (m, 6H).

Example 68: Preparation of 3S-6,7-dihydroxy-1,1-dimethyl-1,2,3,4-tetrahydro-isoquinoline-3-acyl-Lys (Pro-Ala-Glu) (5Ap)

By following the method of Example 53, 173 mg (82%) of the title compound as colorless powder was prepared from 301 mg (0.32 mmol) 3S-6,7-dihydroxy-1,1-dimethyl-1,2,3,4-tetrahydro-isoquinoline-3-acyl-Lys[Boc-Pro-Ala-Glu(OBzl)]-OBzl. Mp 194.7-196.1° C.; $[\alpha]_D^{25}$=−2.3 (c=0.25, CH$_3$OH); ESI-MS (m/e): 661 [M−H]$^-$; IR(KBr): 3053.3, 2945.3, 2370.5, 2320.4, 1651.1, 1546.9, 1533.4, 1448.5, 1388.8, 1240.2, 1165.0, 1045.4, 644.2; $^1$HNMR (300 MHz, D$_2$O) δ/ppm=6.78 (s, 1H), 6.67 (s, 1H), 4.42-4.28 (m, 5H), 3.29 (m, 2H), 3.13 (m, 3H), 2.99 (m, 1H), 2.38 (m, 2H), 2.29 (m, 1H), 1.90 (m, 5H), 1.69 (s, 3H), 1.55 (s, 3H), 1.31 (m, 6H).

Comparative Example 1: Preparation of 3S-6,7-dihydroxy-1,1-dimethyl-1,2,3,4-tetrahydro-isoquinoline-3-acyl-Lys (6)

By following the method of Example 4, 620 mg (85%) of the title compound as light pink solid was prepared from 1.00 g (2.03 mmol) 3S-6,7-dihydroxy-1, 1-dimethyl-1,2,3, 4-tetrahydro-isoquinoline-3-acyl-Lys-OBzl. This compound 6 was used as a control group in the following experimental examples. ESI-MS(m/e): 363[M−H]$^-$.

Experimental Example 1: Evaluating the Thrombolytic Activity of Compounds 5Aa-p of the Present Invention Via Intravenous Administration 1) Evaluation Method 200-220 g male SD rats were anesthetized with 20% urethane solution (6 mL/kg, ip). Anesthetized rats were fixed in a supine position, and the right common carotid artery was separated, clamped at the proximal end with an arterial clip, and penetrated with a suture at the proximal and distal ends, respectively. The suture at the distal end is clipped tightly by a hemostatic clamp at the skin/fur. Cannulation was performed at the distal end, the arterial clamp was loosened, and about 1 ml arterial blood was discharged into a 1 mL EP vial. 0.1 mL rat arterial blood was injected into a vertically fixed glass tube (15 mm in length, with an inner diameter of 2.5 mm and an outer diameter of 5.0 mm, sealed with a rubber stopper at the bottom), into which was immediately inserted a thrombus immobilization screw made of stainless steel. The thrombus immobilization screw, formed by coiling of a stainless steel wire having a diameter of 0.2 mm, had a spiral part of 12 mm in length, including 15 coils each having a diameter of 1.0 mm, and a stem of 7.0 mm in length which was connected to the spiral part and had a question-mark-like shape. 40 min after the blood coagulated, the rubber stopper at the bottom of the glass tube was removed, the stem of the thrombus immobilization screw was fixed by forceps, and the thrombus-wrapped thrombus immobilization screw was carefully taken out from the glass tube and precisely weighted.

A bypass cannula was composed of 3 segments. The middle segment was a polyethylene tube having a length of 60 mm and an inner diameter of 3.5 mm. The segments on both ends were similar polyethylene tubes having a length of 100 mm, an inner diameter of 1 mm and an outer diameter of 2 mm, one end of which was pulled to form a tip, with an outer diameter of 1.0 mm (used in inserting into the rat carotid artery or vein), the other end of which was sheathed by a polyethylene tube having a length of 7 mm and an outer diameter of 3.5 mm (thickened, used in inserting into the polyethylene tube of the middle segment). The inner wall of the 3-segment cannula was entirely silylated. The thrombus-wrapped thrombus immobilization screw was placed into the polyethylene tube of the middle segment, and both ends of the tube sheath the thickened ends of two polyethylene tubes. The cannula was filled with a heparin solution in normal saline (50 IU/kg) through the tip end by using an injector and was ready for use.

The left external jugular vein of the rat was separated and penetrated with a suture at the proximal and distal ends respectively, and the distal end was ligated. An incision was carefully made on the exposed left external jugular vein, and the tip of the bypass cannula prepared as described above was inserted into the proximal end of the incision in the left external jugular vein, away from the stem of the thrombus immobilization screw in the middle segment of the bypass cannula (which accommodated the accurately weighed thrombus immobilization screw). A precise amount of heparin in saline (50 IU/kg) was injected through the tip at the other end by using an injector. At this moment, without removing the injector from the polyethylene tube, the tube between the injector and the polyethylene tube was clamped with a hemostatic clamp. The blood flow was stopped by clamping the proximal end of the right common carotid artery with an arterial clip, and an incision was cut carefully across the common carotid artery near the clip. The injector was pulled out of the polyethylene tube through the tip, and the tip of the polyethylene tube was then inserted into the proximal end of the artery incision. Both ends of the bypass cannula were fixed to the artery or vein with #4 sutures.

A scalp needle was used to pass saline solution, a urokinase in saline solution or varied concentrations of the compounds in saline solution through the middle section of the bypass cannula (which accommodated the accurately weighed thrombus immobilization screw) to a position at the proximal vein and away from the thrombus immobilization screw. The artery clip was then removed to allow blood to flow from the artery to the vein through the bypass cannula. A rat arteriovenous bypass thrombolysis model was thus established. The solution in the injector was slowly injected into blood (about 6 mim), allowing normal saline, urokinase (positive control), or compounds of the present invention to act on the thrombus through blood circulation in the order of vein-heart-artery. The process was timed at the beginning of injection, and the thrombus immobilization screw was removed from the bypass cannula after 1 hour and accurately weighed. The difference in the mass of the thrombus immobilization screw in the rat bypass cannula before and after the administration was determined to evaluate the in vivo thrombolytic activity of compounds. The weight reduction of the thrombus was expressed by average values and standard deviation ($\bar{x}\pm SD$).

2) Administration Method and Dose

The administration method is intravenous injection. The blank control was normal saline solution, and the dose was 3 mL/kg. The positive control was urokinase, and the dose was 20000 U/kg, which was equal to 1.68 mg/kg. The dose of compounds 5Aa-p of the present invention was 0.1 nmol/kg.

3) Evaluation Results

The thrombolytic activity was expressed by the weight reduction of the thrombus ($\bar{x}\pm SD$ mg), and the results were listed in Table 1. Data showed that compounds 5Aa-p at a dose of 0.1 nmol/kg via intravenous administration could effectively lyse the thrombus. ($p<0.01$ compared with normal saline solution). The thrombolytic activities of compounds 5Aa, 5Af, 5Ag, 5Ak, and 5Ao were comparable to that of urokinase at a dose of 20000 U/kg. Among the compounds with higher thrombolytic acitivity, 5Aa, 5Ad, 5Af, 5Ag and 5Ak, compound 5Ak showed the highest thrombolytic activity, thus the dose dependant relationship thereof was further evaluated.

TABLE 1

The thrombolytic activity of compounds 5Aa-p through intravenous injection.

| Compounds | Weight reduction in thrombus | Compounds | Weight reduction in thrombus |
|---|---|---|---|
| normal saline solution | 9.25 ± 1.59 | urokinase | 18.95 ± 2.73[a] |
| 5Aa | 19.35 ± 2.76[b] | 5Ai | 16.00 ± 2.03[a] |
| 5Ab | 17.12 ± 1.64[a] | 5Aj | 15.23 ± 2.45[a] |
| 5Ac | 16.23 ± 2.81[a] | 5Ak | 19.38 ± 2.81[b] |
| 5Ad | 18.11 ± 2.48[b] | 5Al | 14.65 ± 2.86[a] |
| 5Ae | 13.63 ± 1.92[a] | 5Am | 16.65 ± 2.52[a] |
| 5Af | 17.92 ± 1.69[b] | 5An | 16.44 ± 2.32[a] |
| 5Ag | 18.98 ± 2.14[b] | 5Ao | 15.86 ± 2.21[a] |
| 5Ah | 17.10 ± 1.79[a] | 5Ap | 16.03 ± 2.14[a] |

TABLE 1-continued

The thrombolytic activity of compounds 5Aa-p through intravenous injection.

| Compounds | Weight reduction in thrombus | Compounds | Weight reduction in thrombus |
|---|---|---|---|
| 6 | 13.87 ± 3.07[a] | PAK | 14.17 ± 1.84[a] |
| 6 + PAK | 15.37 ± 3.00[a] | | | n = 10;
[a] $p < 0.01$ compared with normal saline solution;
[b] $p < 0.01$ compared with normal saline solution; $p < 0.05$ compared with compound 6, PAK and compound 6 + PAK; $p > 0.05$ compared with urokinase Experimental Example 2: Evaluating the Dose-Effect Relationship for the Thrombolytic Activity of the Compound 5Ak of the Present Invention Via Intravenous Administration Intravenous injection administration was performed according to the method of example 1. The blank control was normal saline solution, and the dose was 3 mL/kg. The positive control was urokinase, and the dose was 20000 U/kg, which was equal to 1.68 mg/kg. The high, medium and low doses of the compound 5Ak were 0.1 nmol/kg, 0.01 nmol/kg, and 0.001 nmol/kg, respectively. The results are listed in Table 2. Data showed obvious dose-effect relationship of compound 5Ak.

TABLE 2

The dose-effect relationship for thrombolysis of the compound 5Ak of the present invention

| Compounds | Weight reduction in thrombus ($\bar{x}$ ± SD mg) |
|---|---|
| normal saline solution, 3 mL/kg | 10.55 ± 2.52 |
| Urokinase, 20000 U/kg | 25.61 ± 3.87 |
| 5Ak, 0.1 nmol/kg | 21.61 ± 4.62[a] |
| 5Ak, 0.01 nmol/kg | 14.62 ± 2.46[b] |
| 5Ak, 0.001 nmol/kg | 11.73 ± 2.15[c] | n = 10;
[a] $p < 0.01$ compared with normal saline solution and 0.01 nmol/kg 5Ak;
[b] $p < 0.01$ compared with normal saline solution and 0.001 nmol/kg 5Ak;
[c] $p > 0.05$ compared with normal saline solution.

Experimental Example 3: Evaluating the Antithrombotic Activity of Compounds 5Aa-p of the Present Invention Via Intravenous Administration 1) Evaluation Method A cannula was composed of 3 segments. The middle segment has a length of 80 mm and an inner diameter of 3.5 mm. The segments on both ends were similar polyethylene tubes having a length of 100 mm, an inner diameter of 1 mm and an outer diameter of 2 mm, one end of which was pulled to form a tip (used in inserting into the rat carotid artery or vein), The inner wall of the 3-segment cannula was entirely silylated. The pre-weighed, 60 mm in length thread was placed in the middle segment of the polyethylene tube. Both ends of the wider tube sheathed the un-narrowed ends of two polyethylene tubes respectively (0.5 mm of the thread was restrained by one of the segment to fix the thread). The cannula was filled with a heparin solution in normal saline (50 IU/kg) through the tip end by using an injector and was ready for use.

200-220 g male SD rats were anesthetized with 20% urethane solution (6 m L/kg, ip). Anesthetized rats were fixed in a supine position, and the left external jugular vein was separated and penetrated with a suture at the proximal and distal ends respectively, and the distal end was ligated. An incision was carefully made on the exposed left external jugular vein, and the tip end without thread-restraining of the bypass cannula prepared as described above was inserted into the proximal end of the open incision in the left external jugular vein. A precise amount of heparin in normal saline (50 IU/kg) was injected through the tip at the other end by using an injector. Then, the injector was replaced, and precise amount of drug was injected by the same way. At this moment, without removing the injector from the ethylene tube, the right common carotid artery was separated, and the proximal end was clipped by an artery clip. The right common carotid artery was penetrated with a suture at the proximal and distal ends respectively, and the distal end was ligated. An incision was carefully cut across the right common carotid artery near the artery clip. The injector was pulled out of the polyethylene tube through the tip, and the tip of the polyethylene tube was then inserted into the proximal end of the artery incision. Both ends of the bypass cannula were fixed to the artery or vein with #4 sutures. The artery clip was then removed to allow blood to flow from the artery to the vein through the bypass cannula. A rat arterio-venous bypass thrombolysis model was thus established. The process was timed from the beginning of circulation, the thread attached with thrombus was taken out from the bypass cannula after 15 minutes and accurately weighed. The difference in the mass of the thread before and after was determined as the wet weight of the thrombus, which was statistically analyzed and used to evaluate the in vivo antithrombotic activities of the compounds. The wet weight of the thrombus was expressed as average value and standard deviation ($\bar{x}\pm SD$).

2) Drug Administration Method and Dose

The drug administration method is intravenous injection. The blank control was normal saline solution, and the dose was 1 mL/kg. The positive control was aspirin, and the dose was 9 mg/kg. The dose of compounds 5Aa-p of the present invention was 0.1 nmol/kg.

3) Results

The antithrombotic activities were expressed as the wet weight of thrombus ($\bar{x}\pm SD$), and the results were listed in Table 3. Data showed that the dose of the compound 5Ak at 0.1 nmol/kg via intravenous administration may effectively inhibit the formation of thrombus (p<0.001, compared with normal saline solution), and the dose dependant relationship of 5Ak with higher activity was thus further evaluated.

TABLE 3

The in vivo antithrombotic experiment of compound 5Aa-p of the present invention via intravenous administration

| Compounds | wet weight of thrombus ($\bar{x} \pm SD$ mg) | Compounds | wet weight of thrombus ($\bar{x} \pm SD$ mg) |
|---|---|---|---|
| NS | 65.40 ± 2.73 | Aspirin | 46.95 ± 5.21[a] |
| 5Aa | 54.04 ± 6.43[a] | 5Ai | 56.12 ± 5.55[a] |
| 5Ab | 54.17 ± 6.61[a] | 5Aj | 50.56 ± 3.96[a] |
| 5Ac | 52.93 ± 3.96[a] | 5Ak | 51.93 ± 2.74[a] |
| 5Ad | 51.91 ± 4.97[a] | 5Al | 54.20 ± 3.93[a] |
| 5Ae | 57.20 ± 6.43[a] | 5Am | 58.14 ± 2.30[a] |
| 5Af | 54.01 ± 4.25[a] | 5An | 55.11 ± 4.76[a] |
| 5Ag | 54.28 ± 3.57[a] | 5Ao | 48.34 ± 3.29[a] |
| 5Ah | 50.67 ± 3.71[a] | 5Ap | 49.97 ± 6.32[a] | n = 10; 5Aa-p (i.v.): 0.1 nmol/kg; Aspirin: 9 mg/kg;
[a]p < 0.001 compared with NS.

Experimental Example 4: Evaluating the Dose-Effect Relationship for Antithrombotic Activity of Compound 5Ak of the Present Invention Via Intravenous Administration 1) Evaluation Method The method was the same as in example 3.

2) Drug Administration Method and Dose

The drug administration method is intravenous injection. The blank control was normal saline solution, and the dose was 3 mL/kg. The positive control was aspirin, and the dose was 9 mg/kg. The high, medium and low doses of the compound 5Ak were 0.1 nmol/kg, 0.01 nmol/kg, and 0.001 nmol/kg respectively.

3) Results

The results were listed in Table 4, and compound 5Ak showed obvious dose-effect relationship.

TABLE 4

In vivo dose-effect realtionship for antithrombotic activity of compound 5Ak of the present invention

| Compounds | wet weight of thrombus ($\bar{x} \pm SD$ mg) |
|---|---|
| NS | 63.46 ± 3.67 |
| Aspirin | 45.62 ± 2.60 |
| 5Ak, 0.1 nmol/kg | 52.16 ± 2.02[a] |
| 5Ak, 0.01 nmol/kg | 57.34 ± 3.73[b] |
| 5Ak, 0.001 nmol/kg | 61.91 ± 3.27[c] | n = 10;
[a]p < 0.01 compared with normal saline solution and 0.01 nmol/kg 5Ak;
[b]p < 0.01 compared with normal saline solution and 0.001 nmol/kg 5Ak;
[c]p > 0.05 compared with normal saline solution.

Experimental Example 5: Evaluating the Therapeutic Effect of the Compound 5Ak of the Present Invention in Stroke Rats For evaluating the therapeutic effect of compounds 5Aa-p in stroke rats, compound 5Ak was selected as a representative and its therapeutic effect in stroke rats was evaluated by the method below.

1) Evaluation Method

SD male rats (280-300 g) were randomly divided to UK positive control group at a dose of 20000 IU/kg, blank control group with normal saline solution, compound control group with PAK at a dose of 5 µmol/kg, and compound 5Ak group at a dose of 1 µmol/kg (high), 0.1 µmol/kg (medium), and 0.01 µmol/kg (low). A 10% chloral hydrate solution (400 mg/kg) was injected intraperitoneally into rats for anesthesia. A vertical incision of about 2 cm in length was made on the right side near the center of the neck, and the right common carotid artery (CCA), external carotid artery (ECA) and internal carotid artery (ICA) were separated along the margin of the inner side of sternocleidomastoid muscles. The incision at the internal carotid artery and the proximal end of the common carotid artery were clipped respectively with noninvasive arterial clips. A small incision was made on the external carotid artery, and the distal end of the external carotid artery was ligated. The arterial clip at the proximal end of the common carotid artery was released, and 10 µl blood was drawn. After blood was drawn, the proximal end of the common carotid artery was again clipped with a noninvasive arterial clip. The 10 µl blood drawn was placed in a 1 mL EP vial and kept at RT for 30 min to allow the coagulation of blood and then transferred into a −20° C. refrigerator for 1 hour to allow the formation of solid coagulation. 1 hour later, the blood clots were taken out, 1 mL normal saline was added therein, and then the blood clots were broken into relatively uniform microthrombus by a steel spatula. The microthrombus suspension was then transferred into a 1 mL injector for use. When the clip on the internal carotid artery of the rat was released, the 1 mL thrombus suspension in the injector was slowly injected from the external carotid artery of the rat to its proximal end, and then was injected into the brain of the rat through the internal carotid artery. Subsequently, the proximal end of the external carotid artery was ligated, the arterial clips on the internal carotid artery and the common carotid artery were released, and blood flow was restored. The common jugular vein was separated, and then injected with UK at the dose of 20000 IU/kg, normal saline solution, or compound 5Ak at the dose of 1 μmol/kg. The vein was ligated. 3 drops of penicillin was dropped on the wound. The wound was sewed, and animals were waited for awake.

24 hours after the rats were awake, the degree of damage in neural function was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were statistically analyzed and subjected to t-test.

After the rats were awake for 24 hours and assessed for their degree of damage in neural function by Zealonga method, they were anesthetized with urethane followed by immediate decapitation and removal of the brain. Brain tissues were kept in a −20° C. refrigerator for 2 hours, and coronal sections of about 2 mm were successively sliced from the prefrontal end for a total of 5 sections and then placed into a 2% TTC solution to incubate without light at 37° C. for 30 min. The color change in brain sections was observed: normal brain tissues were stained red by TTC, while ischemic brain tissues appeared in white. Photographs were taken by using a digital camera and processed with image statistics software, and the volume of infarction in brain tissues and the area of normal brain tissues in the coronal sections were calculated. The ratio of the cerebral infarction volume of each group was statistically calculated and subject to t-test.

2) Evaluation Result

The evaluated data according to the Zealong method after the rats awake were listed in Table 5. The percentages of cerebral infarction volume were listed in Table 6.

TABLE 5

Evaluation by the Zealong method after the rats awake for 24 hours

| Compounds | Neural function scores ($\bar{x} \pm SD$) |
|---|---|
| normal saline solution | 2.90 ± 0.99 |
| urokinase, 20000 IU/kg | 1.30 ± 0.95[a] |
| 5Ak, 1 μmol/kg | 1.10 ± 0.74[a] |
| 5Ak, 0.1 μmol/kg | 1.40 ± 1.07[b] |
| 5Ak, 0.01 μmol/kg | 2.30 ± 0.95[c] |
| PAK, 5 μmol/kg | 2.20 ± 1.60 | n = 9;
[a] $p < 0.05$ compared with normal saline solution and 0.1 μmol/kg 5Ak;
[b] $p < 0.05$ compared with normal saline solution and 0.01 μmol/kg 5Ak;
[c] $p > 0.05$ compared with normal saline solution and 5 μmol/kg PAK

TABLE 6

Percentage of cerebral infarction volume in rats

| Compounds | Percentage of infarction volume ($\bar{x} \pm SD$ %) |
|---|---|
| normal saline solution | 22.99 ± 5.08 |
| urokinase, 20000 IU/kg | 4.60 ± 2.09 |
| 5Ak, 1 μmol/kg | 3.44 ± 1.99[a] |
| 5Ak, 0.1 μmol/kg | 9.88 ± 2.52[b] |
| 5Ak, 0.01 μmol/kg | 18.05 ± 5.77[c] |
| PAK, 5 μmol/kg | 18.36 ± 7.38 | n = 7;
[a] $p < 0.01$ compared with normal saline solution, $p < 0.05$ compared with 0.1 μmol/kg 5Ak, $p > 0.05$ compared with urokinase;
[b] $p < 0.05$ compared with normal saline solution and 0.1 μmol/kg 5Ak;
[c] $p > 0.05$ compared with normal saline solution.

The data shown in Tables 5 and 6 suggested that compound 5Ak may effectively prevent the brain ischemia rats from occurrence of dyskinesia and cerebral infarction. This function of compound 5Ak was dose dependent.

Experimental Example 6: Evaluating the Free Radical Scavenging Activity of Compounds 5Aa-p of the Present Invention 1) Hydroxyl Free Radical Scavenging Activity 11.316 mg DMPO (dimethylpyridine-N-oxide, Sigma) was dissolved in 1 mL of pure water to obtain 0.1 M DMPO solution. 2.78 g $FeSO_4.7H_2O$ was dissolved in 1 mL of pure water to obtain 10 mM solution. 30% medical $H_2O_2$ was diluted to 0.2%.

The first peak height of the OH signal of 2.5 μL $FeSO_4.7H_2O$ solution+2.5 μL DMPO solution+5 μL $H_2O_2$ solution+5 μL water was measured and repeated for 6 times. This peak height defined as the known paek height of OH signal. The first peak height of the OH signal of 2.5 μL $FeSO_4.7H_2O$ solution+2.5 μL DMPO solution+5 μL $H_2O_2$ solution+5 μL solution of one of the compounds 5Aa-p was measured and repeated for 6 times. This peak height defined as the residual peak height of the OH signal scavenged by one of the compounds 5Aa-p.

Scavenging ratio=(known peak height of OH signal−residual peak height of OH signal of compounds 5Aa-p)/known peak height of OH signal 2) NO Radical Scavenging Activity 7.325 mg MGD (N-methyl-glucamine dithiocarbamate, Sigma) was dissolved in 1 mL of pure water to obtain 25 mM MGD solution. 3.475 g $FeSO_4.7H_2O$ was dissolved in 1 mL of pure water to obtain 12.5 mM solution. 25 mg SNAP (S-Nitroso-acetyl penicillamine) was dissolved in 1 mL of pure water to obtain 110 μM green mother liquid, which was diluted 100 folds to obtain 1 μM SNAP solution.

The first peak height of NO signal of 5 μL MGD solution+5 μL $FeSO_4.7H_2O$ solution+5 μL SNAP solution+5 μL water was measured and repeated for 6 times. This peak height defined as the known peak height of NO signal. The first peak height of NO signal of 5 μL MGD solution+5 μL $FeSO_4.7H_2O$ solution+5 μL SNAP solution+5 μL solution of one of the compounds 5Aa-p was measured and repeated for 6 times. This peak height defined as the residual peak height of the NO signal scavenged by one of the compounds 5Aa-p.

Scavenging ratio=(known peak height of NO signal−residual peak height of NO signal of compounds 5Aa-p)/known peak height of NO signal 3) superoxide anionic radical scavenging activity 0.3 g Xanthine was Dissolved in 1 mL of Pure Water to Obtain 0.5 M xanthine solution (milk white color, largely insoluble). Commercially available raw solution of xanthine oxidase was diluted 10 folds to obtain solution of xanthine oxidase. Saturated DETAPAC solution was diluted 20 folds to obtain 0.9 mM solution. 11.316 mg DMPO was dissolved in 1 mL of pure water to obtain 0.1 M DMPO solution.

5 μL DMPO solution+5 μL DETAPAC solution+5 μL xanthine solution+5 μL xanthine oxidase solution+5 μL compounds 5Aa-p solution The first peak height of superoxide anion signal of 5 μL DMPO solution+5 μL DETAPAC solution+5 μL xanthine solution+5 μL xanthine oxidase solution+5 μL water was measured and repeated for 6 times. This peak height defined as the known peak height of superoxide anion signal. The first peak height of superoxide anion signal of 5 μL DMPO solution+5 μL DETAPAC solution+5 μL xanthine solution+5 μL xanthine oxidase solution+5 μL solution of one of compounds 5Aa-p was measured and repeated for 6 times. This peak height defined as the residual peak height of the superoxide anion signal scavenged by one of the compounds 5Aa-p.

Scavenging ratio=(known peak height of superoxide anion signal−residual peak height of superoxide anion signal of compounds 5Aa-p)/known peak height of superoxide anion signal Results were listed in Table 7. Data showed that the $EC_{50}$ of the compounds 5Aa-p for three free radical scavenging activity was 0.4-0.7 mM. Compounds 5Aa-p have obvious free radical scavenging activity.

TABLE 7

$EC_{50}$ of the compounds 5Aa-p for free radical scavenging activity

| Comopounds | •NO | •OH | Superoxide anionic radical |
| --- | --- | --- | --- |
| 5Aa | 5.99 ± 0.38 | 4.59 ± 0.66 | 4.77 ± 0.56 |
| 5Ab | 5.32 ± 0.73 | 4.71 ± 0.71 | 4.71 ± 0.34 |
| 5Ac | 4.63 ± 0.92 | 3.78 ± 0.85 | 3.66 ± 0.71 |
| 5Ad | 4.53 ± 0.41 | 3.69 ± 0.32 | 3.54 ± 0.71 |
| 5Ae | 6.17 ± 0.88 | 4.66 ± 0.47 | 4.81 ± 0.45 |
| 5Af | 5.68 ± 0.95 | 5.44 ± 0.43 | 4.85 ± 0.31 |
| 5Ag | 6.09 ± 0.95 | 4.22 ± 0.61 | 4.67 ± 0.94 |
| 5Ah | 5.23 ± 0.85 | 4.13 ± 0.73 | 4.01 ± 0.72 |
| 5Ai | 5.27 ± 0.90 | 4.95 ± 0.61 | 4.52 ± 0.64 |
| 5Aj | 5.10 ± 0.75 | 4.16 ± 0.28 | 4.17 ± 0.95 |
| 5Ak | 4.99 ± 0.89 | 4.22 ± 0.82 | 3.63 ± 0.94 |
| 5Al | 5.03 ± 0.41 | 4.89 ± 0.32 | 4.14 ± 0.97 |
| 5Am | 6.47 ± 0.88 | 4.66 ± 0.77 | 3.71 ± 0.45 |
| 5An | 6.59 ± 0.89 | 5.72 ± 0.72 | 3.83 ± 0.94 |
| 5Ao | 4.73 ± 0.99 | 3.96 ± 0.48 | 4.35 ± 0.65 |
| 5Ap | 4.77 ± 0.91 | 4.0 ± 0.51 | 4.20 ± 0.73 | n = 6, $EC_{50}$ = X ± SD; compound concentration was X × $10^{-4}$M

Experimental Example 7: TEM Observations of the Compound 5Aa-p of the Present Invention Samples were prepared as $1\times10^{-7}$ M, $1\times10^{-9}$ M, $1\times10^{-11}$ M solution by distillated water, respectively. A small amount (about 10 μl) of the solution was taken and dropped onto the surface of a copper grid with a filter paper placed underneath, for air dry. The morphology and particle size were then observed under transmission electron microscope (JEOL, JEM-1230) and recorded in photographs.

Figure 9:
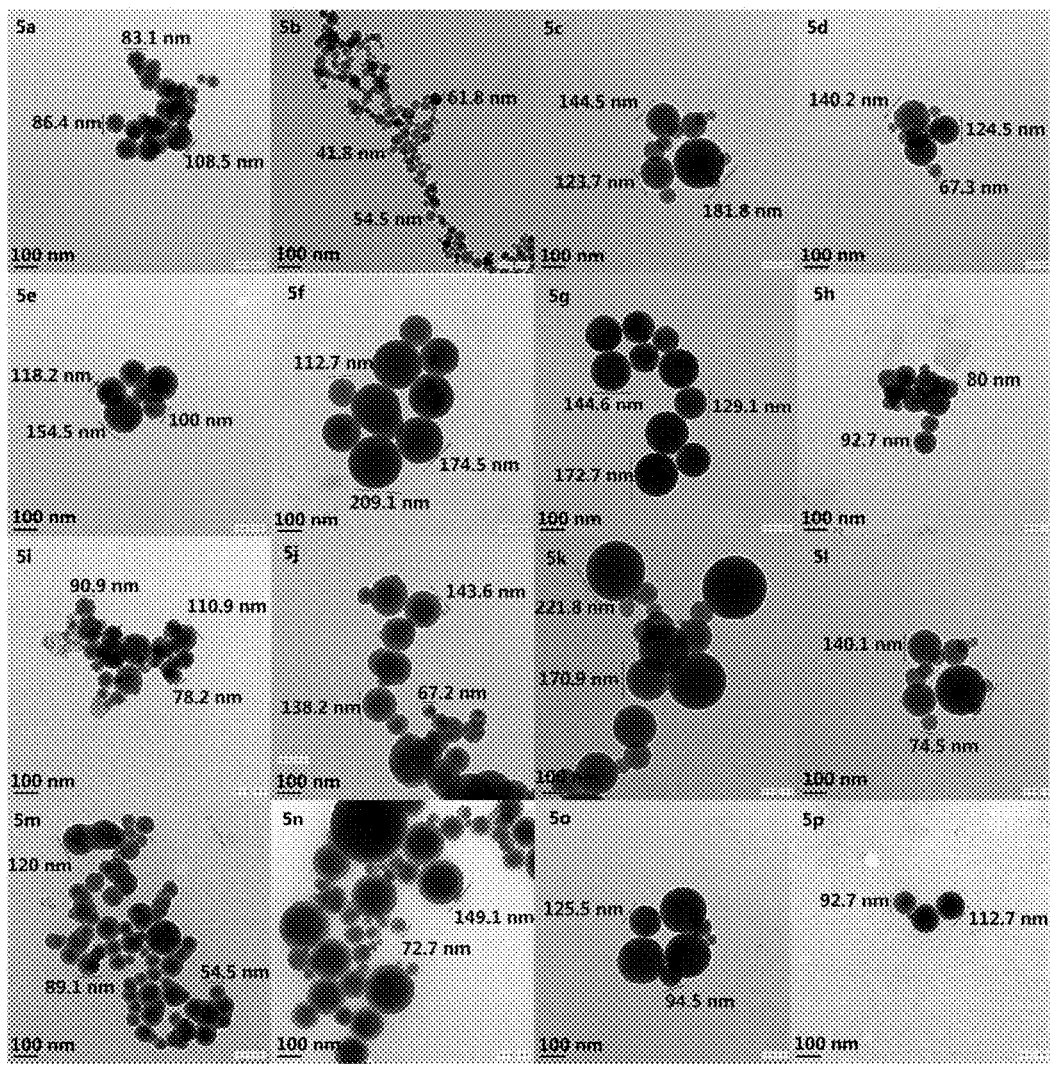
FIG. 9 shows TEM photographs of nanostructures of compounds 5Aa-p according to one embodiment of the present invention.

In aqueous solution, the compounds 5Aa-p may be self-assembled to nanospherical structure having a diameter between 20-210 nm, wherein the diameter was mostly between 20-100 nm. These nanospheres were coupled to various shapes of nanonet or nano necklase, etc. For example, when the in vivo concentration was $1\times10^{-9}$ M (theoritical drug concentration in blood), the TEM photographs were respectively shown (FIG. 9). In FIG. 9, the compounds 5Aa-p were respectively corresponding to figure number 5a, 5b, 5c, 5d, 5e, 5f, 5g, 5h, 5i, 5j, 5k, 5l, 5m, 5n, 5o, and 5p.

Experimental Example 8: Experiment of Successive Treatment with 1 μMol/Kg 5Ak for 6 Times in Stroke Rats after 4 Hours from the Stroke Onset The therapeutic effect was evaluated by neurological functional scores. The lower the score was, the better the therapeutic effect was. A 10% chloral hydrate solution was injected intraperitoneally into male SD rats at a dosage of 400 mg/kg body weight for anesthesia. A longitudinal incision was made at the center of the neck, and the right common carotid artery trunk was separated (about 3 cm in length). External carotid artery branches were each separated and ligated at the hyoid level, and the internal carotid artery was separated from the swollen part of the neck. The incision of the internal carotid artery and the proximal end of the common carotid artery were clipped respectively with noninvasive arterial clips, and the distal end of the external carotid artery was ligated. A catheter containing 0.5 mL thrombus suspension in normal saline was inserted in the external carotid artery trunk. When the clip on the internal carotid artery was released, the 0.5 mL thrombus suspension in normal saline in the catheter slowly flew from the external carotid artery to its proximal end, and then was injected into the arteries in brain through the internal carotid artery. Subsequently, the proximal end of the internal carotid artery was ligated, the arterial clips on the internal carotid artery and the common carotid artery were released, and blood flow was restored. After the wound was stitched up, 20,000 IU penicillin was intramuscularly injected for prevention from infection. 4 hours later, compound 5Ak in normal saline (at the dose of 1 μmol/kg, n=10) was infused for consecutive 6 days and observed for 7 days. Self-comparison was performed each day, and the neurological deficit degree was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were listed in Table 8. Data showed that in rats receiving a successive 6-day treatment with 1 μmol/kg 5Ak once per day after 4 hours from stroke onset, no death occurred. Eight of the ten rats improved to no neurological deficits. Only 2 rats had slight neurological deficits. Therefore, the dose of 1 μmol/kg 5Ak has definite therapeutic effect after 4 hours from stroke onset.

TABLE 8

Therapeutic effect of rats receiving treatment of 1 μmol/kg 5Ak after 4 hours from stroke onset

| Evaluation time | Daily neural function scores (Mean ± SD) and number of rats under each score | | | | | |
| --- | --- | --- | --- | --- | --- | --- |
| | 0 score | 1 score | 2 scores | 3 scores | 4 scores | 5 scores |
| $1^{st}$ day | 3 | 5 | 1 | 1 | 0 | 0 |
| $2^{nd}$ day | 5 | 4 | 1 | 0 | 0 | 0 |
| $3^{rd}$ day | 3 | 6 | 1 | 0 | 0 | 0 |
| $4^{th}$ day | 8 | 1 | 1 | 0 | 0 | 0 |

TABLE 8-continued

Therapeutic effect of rats receiving treatment
of 1 µmol/kg 5Ak after 4 hours from stroke onset

| Evaluation time | Daily neural function scores (Mean ± SD) and number of rats under each score | | | | | |
|---|---|---|---|---|---|---|
| | 0 score | 1 score | 2 scores | 3 scores | 4 scores | 5 scores |
| 5$^{th}$ day | 6 | 4 | 0 | 0 | 0 | 0 |
| 6$^{th}$ day | 8 | 2 | 0 | 0 | 0 | 0 |

TABLE 9

Therapeutic effect of rats receiving treatment
of 1 µmol/kg 5Ak after 6 hours from stroke onset

| Evaluation time | Daily neural function scores (Mean ± SD) and Number of rats under each score | | | | | |
|---|---|---|---|---|---|---|
| | 0 score | 1 score | 2 scores | 3 scores | 4 scores | 5 scores |
| 1$^{st}$ day | 0 | 4 | 4 | 2 | 0 | 0 |
| 2$^{nd}$ day | 0 | 7 | 2 | 1 | 0 | 0 |
| 3$^{rd}$ day | 1 | 6 | 2 | 1 | 0 | 0 |
| 4$^{th}$ day | 4 | 4 | 1 | 0 | 0 | 1 |
| 5$^{th}$ day | 7 | 2 | 0 | 0 | 0 | 0 |
| 6$^{th}$ day | 6 | 3 | 0 | 0 | 0 | 0 |

Experimental Example 9: Experiment of Successive Treatment with 1 µMol/Kg 5Ak for 6 Times in Stroke Rats after 6 Hours from the Stroke Onset The therapeutic effect was evaluated by neurological functional scores. The lower the score was, the better the therapeutic effect was. A 10% chloral hydrate solution was injected intraperitoneally into male SD rats at a dosage of 400 mg/kg of body weight for anesthesia. A longitudinal open incision was made at the center of the neck, and the right common carotid artery trunk was separated (about 3 cm in length). External carotid artery branches were each separated and ligated at the hyoid level, and the internal carotid artery was separated at the swollen part of the neck. The incision in the internal carotid artery and the proximal end of the common carotid artery were clipped respectively with noninvasive arterial clips, and the distal end of the external carotid artery was ligated. A catheter containing 0.5 mL thrombus suspension in normal saline was inserted in the external carotid artery trunk. When the clip on the internal carotid artery was released, the 0.5 mL thrombus suspension in normal saline in the catheter slowly flew from the external carotid artery to its proximal end, and then was injected into the arteries in brain through the internal carotid artery. Subsequently, the proximal end of the internal carotid artery was ligated, the arterial clips on the internal carotid artery and the common carotid artery were released, and blood flow was restored. After the wound was stitched up, 20,000 IU penicillin was intramuscularly injected for prevention from infection. After 6 hours, compound 5Ak in normal saline (at the dose of 1 µmol/kg, n=10) was infused consecutive for 6 days and observed for 7 days. Self-comparison was performed each day, and the neurological deficit degree was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were listed in Table 9. Data showed that in rats receiving a successive 6-day treatment with 1 µmol/kg 5Ak once per day after 6 hours from stroke onset, only one rat died accidentally. Six of the nine rats recovered to no neurological deficits. Only 3 rats had slight neurological deficits. Therefore, the dose of 1 µmol/kg 5Ak has definite therapeutic effect after 6 hours from stroke onset.

Experimental Example 10: Experiment of Successive Treatment with 1 µMol/Kg 5Ak for 6 Times in Stroke Rats after 24 Hours from the Stroke Onset The therapeutic effect was evaluated by neurological functional scores. The lower the score was, the better the therapeutic effect was. A 10% chloral hydrate solution was injected intraperitoneally into male SD rats at a dosage of 400 mg/kg of body weight for anesthesia. A longitudinal incision was made at the center of the neck, and the right common carotid artery trunk was separated (about 3 cm in length). External carotid artery branches were each separated and ligated at the hyoid level, and the internal carotid artery was dissected at the swollen part of the neck. The incisions in the internal carotid artery and the proximal end of the common carotid artery were clipped respectively with noninvasive arterial clips, and the distal end of the external carotid artery was ligated. A catheter containing 0.5 mL thrombus suspension in normal saline was inserted in the external carotid artery trunk. When the clip on the internal carotid artery was released, the 0.5 mL thrombus suspension in normal saline in the catheter slowly flew from the external carotid artery to its proximal end, and then was injected into the arteries in brain through the internal carotid artery. Subsequently, the proximal end of the internal carotid artery was ligated, the arterial clips on the internal carotid artery and the common carotid artery were released, and blood flow was restored. After the wound was stitched up, 20,000 IU penicillin was intramuscularly injected for prevention from infection. After 24 hours, compound 5Ak in normal saline (at the dose of 1 µmol/kg, n=10) was infused consecutive for 6 days and observed for 7 days. Self-comparison was performed each day, and the neurological deficit degree was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were listed in Table 10. Data suggested that 2 rats died after 24 hours from stroke onset. In the rest 8 rats receiving a 6-day successive treatment by using 1 µmol/kg 5Ak once per day, no death occurred. Three of the 8 rats recovered to no neurological deficits. Four rats had slight neurological deficits, and one rat had obvious neurological deficits. Therefore, the dose of 1 µmol/kg 5Ak still has definite therapeutic effect after 24 hours from stroke onset.

TABLE 10

Therapeutic effect of rats receiving treatment of
1 μmol/kg 5Ak after 24 hours from stroke onset

| Evaluation time | Daily neural function scores (Mean ± SD) and number of rats under each score | | | | | |
|---|---|---|---|---|---|---|
| | 0 score | 1 score | 2 scores | 3 scores | 4 scores | 5 scores |
| $1^{st}$ day | 1 | 4 | 0 | 2 | 1 | 0 |
| $2^{nd}$ day | 2 | 3 | 3 | 1 | 0 | 0 |
| $3^{rd}$ day | 3 | 2 | 3 | 0 | 0 | 0 |
| $4^{th}$ day | 2 | 3 | 3 | 0 | 0 | 0 |
| $5^{th}$ day | 4 | 3 | 1 | 0 | 0 | 0 |
| $6^{th}$ day | 3 | 4 | 1 | 0 | 0 | 0 |

TABLE 11

Therapeutic effect of rats receiving treatment of
2.5 μmol/kg 5Ak after 6 hours from stroke onset

| Evaluation time | Daily neural function scores (Mean ± SD) and number of rats under each score | | | | | |
|---|---|---|---|---|---|---|
| | 0 score | 1 score | 2 scores | 3 scores | 4 scores | 5 scores |
| $1^{st}$ day | 1 | 7 | 0 | 1 | 0 | 0 |
| $2^{nd}$ day | 3 | 4 | 2 | 0 | 0 | 0 |
| $3^{rd}$ day | 6 | 2 | 1 | 0 | 0 | 0 |
| $4^{th}$ day | 6 | 3 | 0 | 0 | 0 | 0 |
| $5^{th}$ day | 5 | 4 | 0 | 0 | 0 | 0 |
| $6^{th}$ day | 7 | 2 | 0 | 0 | 0 | 0 |

Experimental Example 11: Experiment of Successive Treatment with 2.5 μMol/Kg 5Ak for 6 Times in Stroke Rats after 6 Hours from the Stroke Onset The therapeutic effect was evaluated by neurological functional scores. The lower the score was, the better the therapeutic effect was. A 10% chloral hydrate solution was injected intraperitoneally into male SD rats at a dosage of 400 mg/kg of body weight for anesthesia. A longitudinal incision was made at the center of the neck, and the right common carotid artery trunk was separated (about 3 cm in length). External carotid artery branches were each separated and ligated at the hyoid level, and the internal carotid artery was separated at the swollen part of the neck. The incision at the internal carotid artery and the proximal end of the common carotid artery were clipped respectively with noninvasive arterial clips, and the distal end of the external carotid artery was ligated. A catheter containing 0.5 mL thrombus suspension in normal saline was inserted in the external carotid artery trunk. At the same time when the clip on the internal carotid artery was released, the 0.5 mL thrombus suspension in normal saline in the catheter slowly flew from the external carotid artery to its proximal end, and then was injected into the arteries in brain through the internal carotid artery. Subsequently, the proximal end of the internal carotid artery was ligated, the arterial clips on the internal carotid artery and the common carotid artery were released, and blood flow was restored. After the wound was stitched up, 20,000 IU penicillin was intramuscularly injected for prevention from infection. After 6 hours, compound 5Ak in normal saline (at the dose of 2.5 μmol/kg, n=10) was infused consecutive for 6 days and observed for 7 days. Self-comparison was performed each day, and the neurological deficit degree was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were listed in Table 11. Data showed that in nine rats receiving a successive 6-day treatment with 2.5 μmol/kg 5Ak once per day after 6 hours from stroke onset, no death occurred. Seven of the nine rats improved to no neurological deficits. One rats had slight neurological deficits. Therefore, the dose of 2.5 μmol/kg 5Ak obviously has better therapeutic effect than 1 μmol/kg 5Ak after 6 hours from stroke onset.

Experimental Example 12: Experiment of Successive Treatment with 2.5 μMol/Kg 5Ak for 6 Times in Stroke Rats after 24 Hours from the Stroke Onset The therapeutic effect was evaluated by neurological functional scores. The lower the score was, the better the therapeutic effect was. A 10% chloral hydrate solution was injected intraperitoneally into male SD rats at a dosage of 400 mg/kg of body weight for anesthesia. A longitudinal incision was made at the center of the neck, and the right common carotid artery trunk was separated (about 3 cm in length). External carotid artery branches were each separated and ligated at the hyoid level, and the internal carotid artery was separated at the swollen part of the neck. The incision in the internal carotid artery and the proximal end of the common carotid artery were clipped respectively with noninvasive arterial clips, and the distal end of the external carotid artery was ligated. A catheter containing 0.5 mL thrombus suspension in normal saline was inserted in the external carotid artery trunk. When the clip on the internal carotid artery was released, the 0.5 mL thrombus suspension in normal saline in the catheter slowly flew from the external carotid artery to its proximal end, and then was injected into the arteries in brain through the internal carotid artery. Subsequently, the proximal end of the internal carotid artery was ligated, the arterial clips on the internal carotid artery and the common carotid artery were released, and blood flow was restored. After the wound was stitched up, 20,000 IU penicillin was intramuscularly injected for prevention from infection. After 24 hours, compound 5Ak in normal saline (dose 2.5 μmol/kg, n=10) was infused consecutive for 6 days and observed for 7 days. Self-comparison was performed each day, and the neurological deficit degree was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were listed in Table 12. The data show that 3 rats died after 24 hours from stroke onset. In the rest seven rats receiving a successive 6-day treatment with 2.5 μmol/kg 5Ak once per day, two rats died. Three rats recovered to no neurological deficits. One rat had slight neurological deficits, and one rat had obvious neurological deficits. Therefore, the dose of 2.5 μmol/kg 5Ak still has certain therapeutic effect after 24 hours from stroke onset.

TABLE 12

Therapeutic effect of rats received treatment of
2.5 μmol/kg 5Ak after 24 hours from stroke onset

| Evaluation time | Daily neural function scores (Mean ± SD) and Number of rats under each score | | | | | |
|---|---|---|---|---|---|---|
| | 0 score | 1 score | 2 scores | 3 scores | 4 scores | 5 scores |
| 1$^{st}$ day | 1 | 4 | 1 | 0 | 1 | 0 |
| 2$^{nd}$ day | 3 | 2 | 1 | 1 | 0 | 0 |
| 3$^{rd}$ day | 3 | 2 | 1 | 0 | 0 | 1 |
| 4$^{th}$ day | 2 | 2 | 1 | 1 | 0 | 0 |
| 5$^{th}$ day | 4 | 0 | 1 | 0 | 0 | 1 |
| 6$^{th}$ day | 3 | 1 | 1 | 0 | 0 | 0 |

Experimental Example 13: Experiment of Successive Treatment with 5 μMol/Kg 5Ak for 6 Times in Stroke Rats after 24 Hours from the Stroke Onset The therapeutic effect was evaluated by neurological functional scores. The lower the score was, the better the therapeutic effect was. A 10% chloral hydrate solution was injected intraperitoneally into male SD rats at a dosage of 400 mg/kg of body weight for anesthesia. A longitudinal incision was made at the center of the neck, and the right common carotid artery trunk was separated (about 3 cm in length). External carotid artery branches were each separated and ligated at the hyoid level, and the internal carotid artery was separated at the swollen part of the neck. The incision in the internal carotid artery and the proximal end of the common carotid artery were clipped respectively with noninvasive arterial clips, and the distal end of the external carotid artery was ligated. A catheter containing 0.5 mL thrombus suspension in normal saline was inserted in the external carotid artery trunk. When the clip on the internal carotid artery was released, the 0.5 mL thrombus suspension in normal saline in the catheter slowly flew from the external carotid artery to its proximal end, and then was injected into the arteries in brain through the internal carotid artery. Subsequently, the proximal end of the internal carotid artery was ligated, the arterial clips on the internal carotid artery and the common carotid artery were released, and blood flow was restored. After the wound was stitched up, 20,000 IU penicillin was intramuscularly injected for prevention from infection. After 24 hours, compound 5Ak in normal saline (at the dose of 5 μmol/kg, n=10) was infused consecutive for 6 days and observed for 7 days. Self-comparison was performed each day, and the degree of damage of neurological deficit degree was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were listed in Table 13. The data show that one rat died after 24 hours from stroke onset. In the rest ten rats receiving a successive 6-day treatment with 5 μmol/kg 5Ak once per day, no death occurred. Seven rats recovered to no neurological deficits. Three rats had slight neurological deficits. Therefore, the dose of 5 μmol/kg 5Ak has definite therapeutic effect after 24 hours from stroke onset, and obviously better than the dose of 2.5 μmol/kg.

TABLE 13

Therapeutic effect of rats receiving treatment of
5 μmol/kg 5Ak after 24 hours from stroke onset

| Evaluation time | Daily neural function scores (Mean ± SD) and number of rats under each score | | | | | |
|---|---|---|---|---|---|---|
| | 0 score | 1 score | 2 scores | 3 scores | 4 scores | 5 scores |
| 1$^{st}$ day | 0 | 5 | 4 | 0 | 1 | 0 |
| 2$^{nd}$ day | 2 | 6 | 2 | 0 | 0 | 0 |
| 3$^{rd}$ day | 2 | 6 | 2 | 0 | 0 | 0 |
| 4$^{th}$ day | 5 | 5 | 0 | 0 | 0 | 0 |
| 5$^{th}$ day | 6 | 4 | 0 | 0 | 0 | 0 |
| 6$^{th}$ day | 7 | 3 | 0 | 0 | 0 | 0 |

According to the experimental results, the compounds of the present invention may form nanostructure to achieve the functions of crossing the blood-brain barrier. In addition to thrombolytic and antithrombotic functions, these compounds may also effectively scavenge OH, NO, superoxide anionic and other free radical. Moreover, only low dose was needed for effective thrombolysis. A higher dose may demonstrate excellent effect in treating stroke beyond 4 hours from stroke onset. Therefore, these compounds have good prospects for clinical application.

The invention claimed is:

1. A compound having the following formula of Ia:

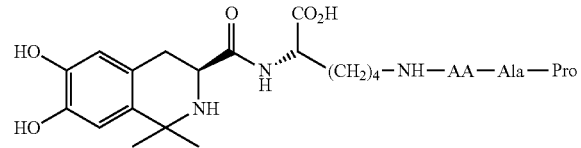

wherein AA is selected from the group consisting of L-Ala, L-Val, L-Trp, L-Tyr, L-Pro, L-Phe, Gly, L-Ser, L-Ile, L-Thr, L-Lys, L-Leu, L-Gln, L-Asn, L-Asp, and L-Glu.

2. The compound of claim 1, wherein AA is L-Lys.

3. A pharmaceutical composition, comprising the compound of claim 1, and a pharmaceutically acceptable carrier.

4. The pharmaceutical composition of claim 3, wherein the compound is in the form of a nanospherical structure.

5. A method for performing thrombolysis, NO free radical scavenging or antithrombotic therapy in a subject in need thereof, the method comprising administering to the subject a pharmaceutically effective amount of the pharmaceutical composition of claim 3.

6. A method of treating stroke or cerebral infarction, the method comprising administering to a subject in need thereof a pharmaceutically effective amount of the pharmaceutical composition of claim 3.

* * * * *

UNITED STATES PATENT AND TRADEMARK OFFICE
CERTIFICATE OF CORRECTION

PATENT NO. : 9,890,193 B2
APPLICATION NO. : 14/956723
DATED : February 13, 2018
INVENTOR(S) : Shi-Qi Peng et al.

Page 1 of 2

It is certified that error appears in the above-identified patent and that said Letters Patent is hereby corrected as shown below:

In the Specification

Column 3, Lines 7-67, Formulae Ia-Ih should be deleted and replaced with the following formulae:

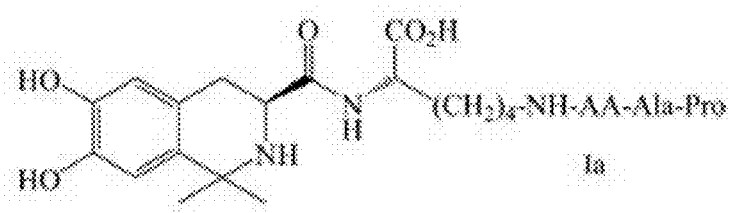

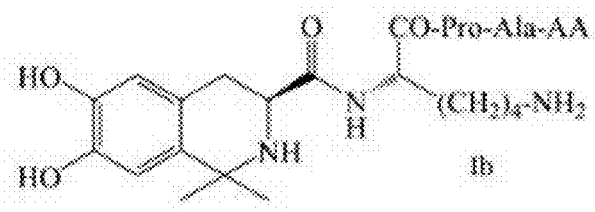

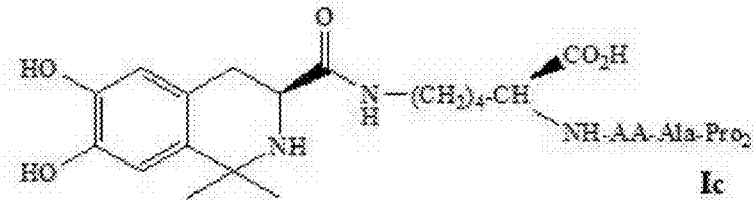

Signed and Sealed this
Tenth Day of April, 2018

Andrei Iancu
*Director of the United States Patent and Trademark Office*

CERTIFICATE OF CORRECTION (continued)
U.S. Pat. No. 9,890,193 B2

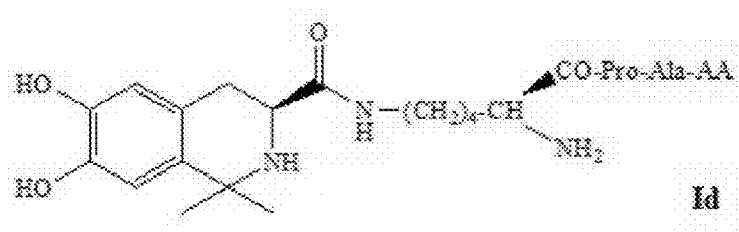

Id

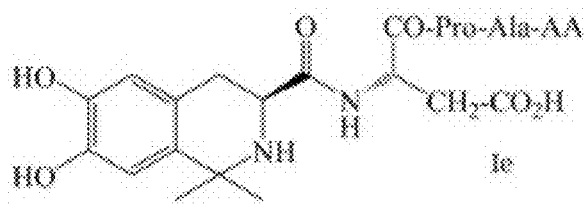

Ie

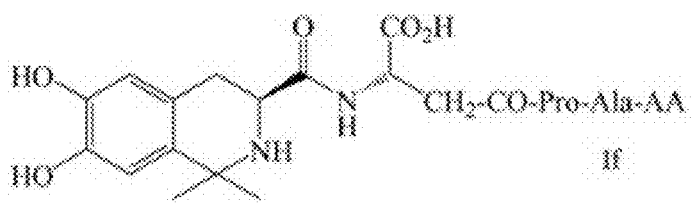

If

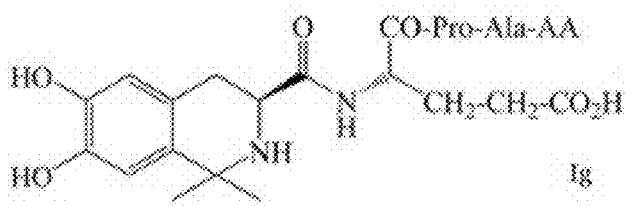

Ig

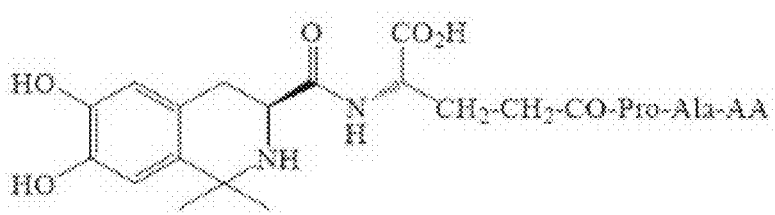

Ih